(12) United States Patent
Kyhse-Andersen et al.

(10) Patent No.: US 10,183,969 B2
(45) Date of Patent: Jan. 22, 2019

(54) METHOD FOR PURIFICATION OF TARGET POLYPEPTIDES

(75) Inventors: Jan Kyhse-Andersen, Værløse (DK); Lars Winther, Smoerum (DK)

(73) Assignee: CHRETO ApS, Væløse (DK)

( * ) Notice: Subject to any disclaimer, the term of this patent is extended or adjusted under 35 U.S.C. 154(b) by 0 days.

(21) Appl. No.: 13/319,261

(22) PCT Filed: May 4, 2010

(86) PCT No.: PCT/EP2010/056010
§ 371 (c)(1),
(2), (4) Date: Nov. 7, 2011

(87) PCT Pub. No.: WO2010/128033
PCT Pub. Date: Nov. 11, 2010

(65) Prior Publication Data
US 2012/0071633 A1    Mar. 22, 2012

Related U.S. Application Data

(60) Provisional application No. 61/177,872, filed on May 13, 2009.

(30) Foreign Application Priority Data

May 7, 2009    (EP) ..................... 09159710

(51) Int. Cl.
*C07K 1/22* (2006.01)
*C07K 1/36* (2006.01)
*C07K 1/32* (2006.01)

(52) U.S. Cl.
CPC .................. *C07K 1/22* (2013.01); *C07K 1/32* (2013.01); *C07K 1/36* (2013.01)

(58) Field of Classification Search
None
See application file for complete search history.

(56) References Cited

U.S. PATENT DOCUMENTS 5,169,936 A * 12/1992 Staples et al. ................ 530/350
5,328,985 A    7/1994 Sano
6,083,709 A *  7/2000 Reynolds et al. ........... 435/7.94
2005/0079554 A1 *  4/2005 Watson et al. ................ 435/7.5
2006/0134705 A1 *  6/2006 Sundrehagen ... G01N 33/54346
                                                                435/7.2
2007/0218535 A1 *  9/2007 Lin et al. ...................... 435/226

FOREIGN PATENT DOCUMENTS

WO    20010053325 A2    7/2001
WO    20050047317 A1    5/2005
WO    20090062942 A2    5/2009

OTHER PUBLICATIONS

DeChancie et al. (J Am Chem Soc. May 2, 2007; 129(17): 5419-5429).*
BioRad (Protein Interaction Analysis, Tech Note, 2009).*
Ramos-Vara et al. (When Tissue Antigens and Antibodies Get Along: Revisiting the Technical Aspects of Immunohistochemistry—The Red, Brown, and Blue Technique, Veterinary Pathology, published on Oct. 15, 2013).*
Hilbrig et al. (Utilization of Group Specific Ligands in the Downstream Processing of Proteins by Affinity Precipitation, Trans IChemE, Part C, Food and Bioproducts Processing, 2006, 84(C1): 28-36).*
Laitinen et al. (Genetically engineered avidins and streptavidins, Cell. Mol. Life Sci. 63 (2006) 2992-3017).*
Hytonen et al., Proteins: Structure, Function and Bioinformatics 61 (3), 597-607 (2005).

* cited by examiner

*Primary Examiner* — Suzanne M Noakes
*Assistant Examiner* — Jae W Lee
(74) *Attorney, Agent, or Firm* — McHale & Salvin, P.A.

(57) ABSTRACT

The present invention relates to a process for purification of a target molecule, comprising the steps: (a) contacting a target molecule, and a population of target binding polypeptides (TBP), in solution for a sufficient time to allow complex formation; and (b) isolating the target from the complex from (a) by subsequent purification steps, wherein (i) the target binding polypeptides have at least two binding functionalities; a first binding functionality towards the target and a second binding functionality towards a catching ligand comprised in a solid support; and (ii) the first binding functionality comprises at least two binding sites for the target, and the target comp¬ rises at least two binding sites for the TBP.

17 Claims, 8 Drawing Sheets

| Conjugate No | A mg/ml | B eq. | C Sub Degree | D mg/ml | E eq. | F eq. | G mg/ml | H min. |
|---|---|---|---|---|---|---|---|---|
| 1 | 10 | 5,0 | 1,3 | 15 | 5,0 | 1 | 2,0 | 120 |
| 2 | 10 | 5,0 | 1,3 | 15 | 5,0 | 2 | 4,1 | 120 |
| 3 | 10 | 5,0 | 1,4 | 15 | 5,0 | 1 | 2,0 | 120 |
| 4 | 10 | 5,0 | 1,4 | 15 | 5,0 | 1 | 2,0 | 30 |
| 5 | 10 | 2,5 | 0,6 | 15 | 2,5 | 1 | 2,0 | 30 |
| 6 | 10 | 2,5 | 0,6 | 15 | 2,5 | 1 | 2,0 | 15 |
| 7 | 10 | 2,5 | 0,7 | 15 | 2,5 | 1 | 1,3 | 30 |
| 8 | 10 | 2,5 | 0,7 | 15 | 2,5 | 1 | 0,7 | 30 |
| 9 | 10 | 2,5 | 0,7 | 15 | 2,5 | 2 | 2,7 | 30 |
| 10 | 10 | 2,5 | 0,7 | 15 | 2,5 | 2 | 1,3 | 30 |
| 11 | 10 | 5,0 | 1,2 | 15 | 5,0 | 1 | 2,1 | 120 |
| 12 | 20 | 10,0 | 4,1 | 20 | 10,0 | 1 | 2,0 | 120 |
| 13 | 20 | 10,0 | 4,1 | 20 | 10,0 | 2 | 4,0 | 120 |
| 14 | 20 | 10,0 | 4,1 | 20 | 10,0 | 3 | 6,0 | 120 |
| 15 | 15 | 5,0 | 2,1 | 15 | 5,0 | 3 | 6,0 | 120 |
| 16 | 15 | 2,5 | 0,9 | 15 | 2,5 | 3 | 6,0 | 120 |
| 17 | 10 | 10,0 | 6,0 | 15 | 10,0 | 1 | 2,0 | 120 |

Fig. 1

METHOD FOR PURIFICATION OF TARGET POLYPEPTIDES

CROSS-REFERENCE TO RELATED APPLICATIONS

This application is a 35 U.S.C. 371 national application of PCT/EP2010/056010 filed May 4, 2010, which claims priority or the benefit under 35 U.S.C. 119 of European application no. 09159710.4 filed May 7, 2009 and U.S. provisional application No. 61/177,872 filed May 13, 2009, the contents of which are fully incorporated herein by reference.

FIELD OF THE INVENTION

The present invention relates to a process for purification of a target molecule, comprising the steps: (a) contacting a target molecule, and a population of target binding polypeptides (TBP), in solution for a sufficient time to allow complex formation; and (b) isolating the target from the complex from (a) by subsequent purification steps.

BACKGROUND OF THE INVENTION

Recovery and purification of therapeutic proteins accounts for approximately 75% of the manufacturing costs of biological drugs. Improving the efficiency and/or reducing cost in the purification step is of general interest. The general industrial purification process often includes a number of unit operation steps, like extraction, precipitation, as well as anion- and cation-exchange chromatography. Affinity chromatography is the preferred downstream process step due to its high recovery, yield and specificity, but the current cost and limitations of affinity chromatography is very substantial and in many cases prohibitive for a more general and efficient use of this unit operation.

Conventional affinity chromatography is in general characterized by having a capturing ligand immobilised to a solid phase matrix. The ligand reversibly binds a target molecule present in a fluid such as liquid culture medium or serum. Target molecules are recovered by dissociating the complex at eluting conditions. Commercially available affinity matrices are in a ready to use format including capturing ligands covalently attached to the matrices. In conventional affinity chromatography the dissociation constant, $K_D$, between the ligand and the target protein is in the range of about $10^{-5}$-$10^{-7}$M. Interactions with dissociation constants exceeding $10^{-10}$-$10^{-11}$M are often impossible to use, as the conditions required to dissociate the complex are then the same as those that will result in denaturation of the target proteins.

In the co-pending application WO 2009062942 we have previously demonstrated the feasibility of applying a generic capturing ligand immobilised to a matrix, and a semi generic dual affinity polypeptide with different binding affinity toward the target biomolecule and the capturing ligand respectively in a purification process. The dual affinity polypeptide (DAP) reacts with the target biomolecule to form a 1:1 complex of medium binding affinity in which one DAP binds to one target, and this complex subsequently binds non-covalently to a generic affinity matrix with a strong binding affinity. The target molecule is recovered by specific elution from the generic matrix leaving the dual affinity polypeptide attached to the capturing ligand on the matrix, due to the tight binding to the ligand preventing leakage from the solid phase matrix.

It is the goal of the present invention to further improve this system by increasing the binding capacity of the DAP molecule.

SUMMARY OF THE INVENTION

The invention provides an improved process for purification of a target molecule using a target binding polypeptide (TBP) which like the DAP molecule has dual binding affinities; one against the target molecule and another against a solid support. The TBP of the invention has been improved over the DAP in that the TBP is capable of forming higher order complexes with the target molecule thus resulting in an increased binding efficiency.

In a first aspect the present invention relates to a process for purification of a target molecule, comprising the steps: (a) contacting a target molecule, and a population of target binding polypeptides (TBP), in solution for a sufficient time to allow complex formation; and (b) isolating the target from the complex from (a) by subsequent purification steps, wherein (i) the target binding polypeptides have at least two binding functionalities; a first binding functionality towards the target and a second binding functionality towards a catching ligand comprised in a solid support; and (ii) the first binding functionality comprises at least two binding sites for the target, and the target comprises at least two binding sites for the TBP.

In a second aspect the present invention relates to a use of an assay capable of measuring complex formation for optimization of the binding capacity of a specific TBP-target combination.

In a third aspect the present invention relates to a TBP for purification of a target molecule, wherein (i) the target binding polypeptide have at least two binding functionalities; a first binding functionality towards the target and a second binding functionality towards a catching ligand comprised in a support; and (ii) the first binding functionality comprises at least two binding sites for the target.

In a forth aspect the present invention relates to a kit for optimization of complex formation comprising a suitable TBP and support material for removing the TBP.

In a fifth aspect the present invention relates to a method for selecting a TBP suitable for complex formation with a target polypeptide of interest comprising: (a) contacting individual TBPs obtainable from a library of TBPs with the target of interest, and (b) determining complex formation.

BRIEF DESCRIPTION OF DRAWINGS

FIG. 1 shows a table summarizing the prepared conjugates with respect to concentrations, stoichiometry, reaction time and the measured degree of SPDP substitution per ProteinA Column A: Protein A concentration during SPDP activation in mg/ml
Column B: Equivalent SPDP per Protein A
Column C: Degree of SPDP substitution per ProteinA
Column D: Avidin concentration during SMCC activation in mg/ml
Column E: Equivalent SMCC per Avidin
Column F: Molar ratio between ProteinA and Avidin during inter conjugation
Column G: Protein A concentration during inter conjugation in mg/ml
Column H: Interconjugation reaction time in minutes.

DETAILED DESCRIPTION OF THE INVENTION

Figure 2:
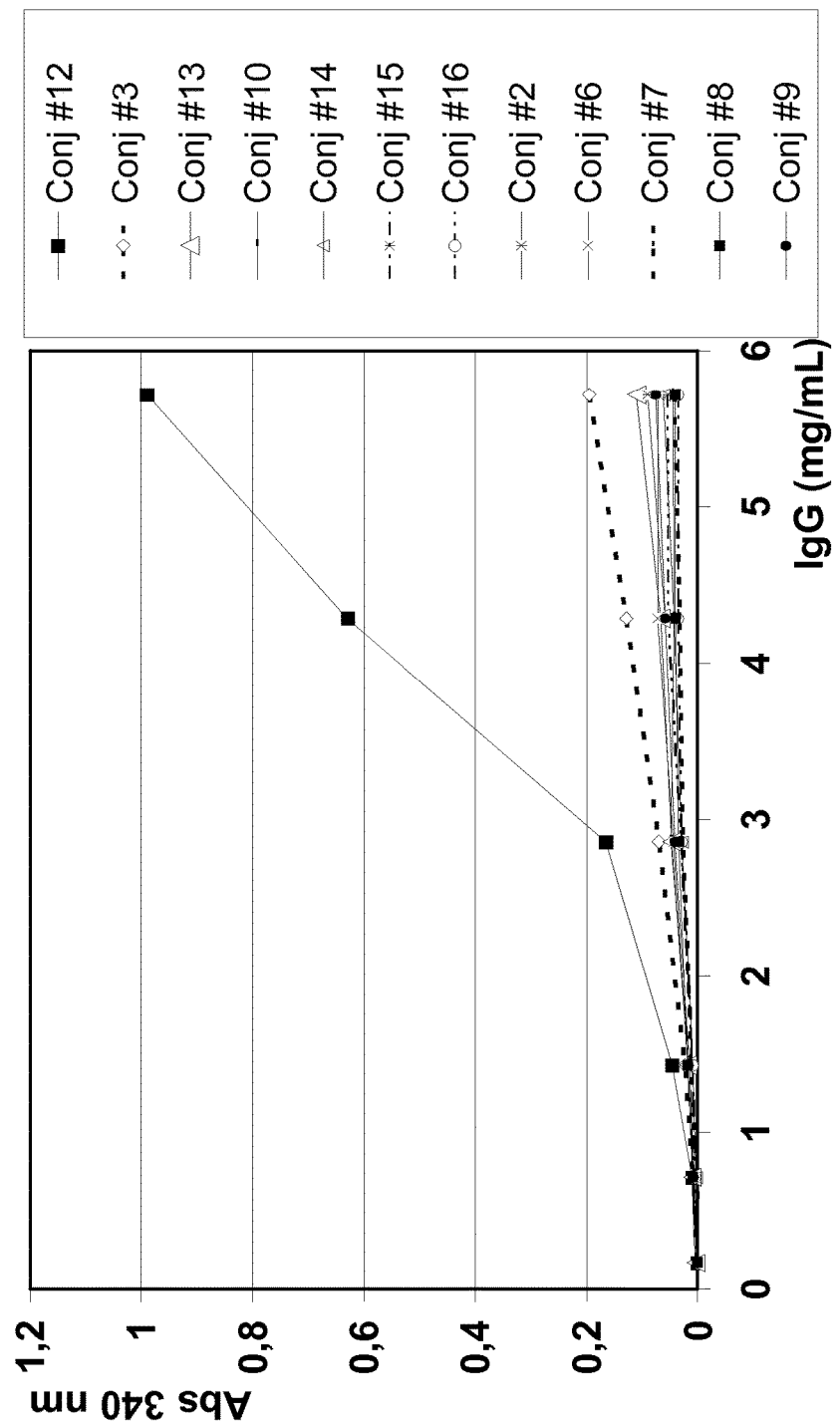
FIG. 2 shows the dose response curve from the turbidimetry assay showing the absorbance at 340 nm after subtraction of blank versus the IgG concentration for crude TBPs before size exclusion chromatography purification. The TBPs was diluted to approximately 2.0 mg/ml.

In the conventional affinity chromatography for purification of e.g. monoclonal antibodies, the capturing ligand (Protein A) is attached to a solid phase matrix and has the affinity towards the target biomolecule (monoclonal antibodies). The DAP technology previously described in WO 2009062942 provides advantages compared to conventional affinity purification technologies for the downstream processing industry due to lower costs, high capacity and ease of use without compromising the quality of the downstream process. An essential feature of the DAP technology is the use of a dual affinity polypeptide as a linker between the target molecule and the solid support comprising a ligand. These dual affinity polypeptides are particularly useful for the downstream processing of biopharmaceutical and diagnostic proteins and peptides. For this technique to be a competitive alternative to the conventional affinity chromatography it is very important that the capacity of the binding of the molecule target to the dual affinity polypeptide (DAP) is optimized. The present invention relates to this optimization and describes which parameters that can advantageously be adjusted in order to optimize said binding capacity. In the following the term target binding polypeptide (TBP) will be used instead of the term DAP.

The inventors of the present invention have surprisingly discovered that when the TBP-molecule binds to the target molecule under certain conditions it is possible to form higher order complexes greatly increasing the binding capacity of the TBP. The formation of these complexes lead to a change in the optical density of the solution and may conveniently be measured by spectrophotometry. It has further been found that such complex formation can be promoted by providing certain minimal binding properties to the TBP as well as optimizing the ratio between the TBP and the target as well as the binding conditions.

As a result of the complex formation between the TBP and the target, this facilitates the application of many subsequent conventional purification steps like centrifugation and precipitation to be applied in the purification of the target, thus eliminating several of the constraints in current purification processes.

According to the invention the minimal structural properties of the TBPs which are necessary in order to result in the formation of higher order complexes requires that the TBPs comprise at least two binding sites for the target, and the target comprises at least two binding sites for the TBP. Furthermore the TBP needs to have at least two binding functionalities; one towards the target and one towards a catching ligand comprised in a support, since in order to eventually isolate the target molecule the TBP needs to be removed by attachment to a support. One aspect of the invention thus relates to a TBP for purification of a target molecule, wherein (i) the target binding polypeptide have at least two binding functionalities; a first binding functionality towards the target and a second binding functionality towards a catching ligand comprised in a support; and (ii) the first binding functionality comprises at least two binding sites for the target.

A main aspect of the invention relates to a process for purification of a target molecule, comprising the steps: (a) contacting a target molecule, and a population of target binding polypeptides (TBP), in solution for a sufficient time to allow complex formation; and (b) isolating the target from the complex from (a) by subsequent purification steps, wherein (i) the target binding polypeptides have at least two binding functionalities; a first binding functionality towards the target and a second binding functionality towards a catching ligand comprised in a support; and (ii) the first binding functionality comprises at least two binding sites for the target, and the target comprises at least two binding sites for the TBP.

In a further embodiment the TBPs comprise at least three binding sites for the target and/or the target comprises at least three binding sites for the TBPs. This feature allows the formation of complex networks leading to an increase in binding capacity of TBP and target.

The population of target binding polypeptides may in one embodiment contain only identical TBPs and may in another embodiment comprise TBPs that are structurally and/or functionally different. In other words the TBPs may in the latter embodiment be a population of TBPs where e.g. the number of target binding sites on each TBP varies within the population and/or the recognition sites specific for each binding site may be different, i.e. the binding sites on the TBP recognizes differently positioned sites on the target.

The complex according to the invention should be distinguished from the more simple complex form that will result from the binding of one target molecule to one TBP. The complex according to the invention should be understood as a higher order complex between the target molecule and the target binding polypeptide (TBP) which is formed in a reversible process, resulting in the formation of a three dimensional network in which bonds between the components are dynamically being formed and broken. Ideally, the network is formed by more than one bridging point per component. It may take some time before equilibrium is obtained between the complex and free components in solution and also internally in the complex. The resulting complex can stay in solution or may precipitate. The formed complex will have a molecular weight significantly higher than the individual components and will consequently have changed solubility properties. It should further be clear that for the complex of the invention the binding strength between target molecule and TBP should be weak enough to be practically reversible in order to recover the target molecule unaltered after subsequent separation steps. For more details see description further below.

The complexes formed according to the invention may conveniently be determined by assays capable of determining changes in optical density or light scatter. Protein and other bio-molecule complex formations can be monitored by light scattering. The complexes act as small particles or spheres in solution. The interaction between electromagnetic radiation in the form of light and the induced electric dipole in spherical particles can cause scatter, which is described in general in the Lorenz-Mie-Debye theory. Turbidimetry and nephelometry are convenient and practical measurement methods for monitoring light scatter from samples in a measurement cell.

In turbidimetry, the light detector is aligned with the measurement cell and the light source. The detector responds to the decreased intensity of the incident light that is caused by scattering in the measurement cell. The output data are analogous to traditional absorption measurements. The only difference is the light scatter phenomenon that causes the decreased light intensity. The decreased intensity is related to the concentration and nature of the scattering spheres in the measurement cell at a constant wavelength.

In nephelometry the light detector is not aligned with the light source and measures the scattered light, rather than the decrease in intensity of the incident radiation as in turbidimetry.

It should be understood that the intensity of scattered light depends on multiple factors, including the wave length of the incident light, the angle from where the detector is placed and the size, degree of solvatization, density, concentration and refractive index of the sphere in solution. Also, if the sphere or complex precipitates from the solution due to growing size and density, the turbidimetry signal can change as less light is scattered despite the presence of formed complex.

Automated turbidimeter, nephelometer and combined instruments are widely used for quantifying protein complexes in immunoassays; in particular complexes between antigen and antibodies or antibody bound latex particles.

Other methods of measuring the complex formation include for example observing the visual change in turbidity against a dark surface, various Raman or Rayleigh scattering methods, electron and near field optical microscopy studies, isolating and measuring the weight of the complex, gradient centrifugation, diffusion speed on or through gels and membranes or measuring the reflection of ultrasonic or other acoustic waves.

The present inventors have realized that formation of the complex between TBP and the target molecule during the purification process can easily be monitored by turbidimetry. In a particular embodiment, complex formation is equivalent to a change in optical density of at least 0.1 when measured by turbidimetry in a solution when target and TPB is mixed and allowed to react. In one particular embodiment the reaction time and temperature is between 1 to 20 min at 25° C., more particularly between 2 to 12 min at 25° C. It should be understood that the reaction time should be sufficient for complexes to form, but longer reaction times are also possible.

The inventors of the present invention have discovered that yield and quality of purification of the target molecule depend to the magnitude of initial complex formation and the ratio between target and TBP. The above turbidimitry assay can be used to optimize the starting ratio between TBP and target in order to maximize complex formation by e.g. performing a simple dose response experiment. This is of importance, as the concentration of target may not be known in advance. Additionally, the optimization of the purification process can be done based on a simple measurement prior to and/or during the purification process by monitoring and controlling the ratio at the optimal level.

Therefore, in a particular embodiment of the invention the ratio of target polypeptide to TBP is optimized to allow optimal complex formation. In particular the process according to the invention is optimized by measuring complex formation. One aspect of the invention therefore relates to a use of an assay capable of measuring complex formation for optimization of the binding capacity of a specific TBP-target combination.

Said measurement is in one embodiment performed by spectrophotometric assays. Such assays preferably include turbidimetry and nephelometry. In a further embodiment the ratio of target to TBP is monitored and controlled during the complex formation step. In an even further embodiment the ratio of target to TBP is monitored before, during, and after the complex formation step.

Preferably, the target recovery is optimized by measuring the amount of TBP-Target complex formed, separated and dissolved.

The measurement can be done directly in place during the process or based on samples taken out. A corrective or optimizing feed back mechanism or instruction is preferred. Even more preferred are automatic feed back mechanisms which based on the change of turbidity before and after mixing target and TBP can control the formation of the complexes of the invention.

The TBP molecule can also be directly detected and monitored using specific binding proteins or physical in place methods or in a separate assay, e.g. ELISA. It can be especially important to detect any TBP traces in the collected and purified target. Also, the TBP can comprise a tag which can be detected directly in line or off line at any point in the purification workflow process. The tag can be detected by spectrophotometry methods or more preferably detected by fluorescence or UV/VIS spectrophotometry. Fluorescent tags which can be incorporated as fusion proteins into recombinantly expressed TBP's are of special relevance.

Preferable fluorescent tags include green fluorescent protein (GFP), cyan fluorescent protein, KFP red, PS-CFP, PS-CFP2, HcRed1, DsRed, Luciferase or other fluorescent or luminescence fusion proteins or indirectly fluorescent tags, like the HaloTag.

The dose-response graph is the basis for numerous immunoassays, including turbidimetry assays. A typical dose-response curve is an X-Y graph relating the concentration of the target molecule to the response of the TBP. The response may be physically measurable. Of particular relevance for the present invention, the response is a change in turbidimetry due to light scatter. Studying and optimizing assays is known to the skilled artist. Numerous books give guidance including (*Immunoassay*, Eleftherios P. Diamandis, Theodore K. Christopoulos, Academic Press, 1996).

The nature and shape of the dose-response curve is the result of the specific reaction between target molecule and TBP and the law of mass action. For a particular concentration of TBP, the change in absorbance or turbidity (Y axis) can be drawn against the concentration of target molecule (x axis). The resulting dose response curve is typically bell shaped or sigmoid. At low target concentration the turbidity is low, as the TBP is in large excess and complexes cannot be formed. At the highest point, the apparent equivalence point, the ratio between targets and TBP result in the largest complex scatter. Beyond the equivalence point, the turbidity decreases, as the target molecule is in excess, tipping the balance for optimum formation of complexes. The dose response behaviour also illustrates the dynamic nature of the complex formation.

A change in the target-to-TBP ratio will result in a new complex distribution and turbidity at the new equilibrium situation.

According to a further advantageous embodiment of to the present invention, the specific recognition and binding of target molecule can be monitored and optimized in solution, in contrast to conventional column-based affinity purification systems.

The optimization of TBP-to-target ratio is also important for cost and best dimensional design reasons, as the TBP is not to be recycled and is therefore a single use reagent.

In addition to the ratio of target to TBP as discussed above, it has been found that the reaction conditions present during the complex formation will also influence the complex formation. In particular certain buffers have been found to promote such complex formation.

Buffer systems suited for increasing, for example, the specific antibody-antigen complex formation is known from immunoassays like turbidimetry, nephelometry and agglutination assays.

Buffers suitable for increasing complex formation according to the invention include reagents for i) lowering the water activity, ii) pH stabilizing and iii) preventing unspecific or random protein interactions and precipitation and increasing the general protein solubility.

More specifically, the water activity reducing components can be taken from the family of low molecular weight salts, polysugars, polyalcohols and other polymers.

In a particular embodiment reagents for lowering water activity comprises ammonium sulphate, caprylic acid, dextran, poly ethylene glycol (PEG), polyvinyl alcohol (PVA), hyaluronic acid, chitosan and their esters, globular polyols like ficoll and polyvinyl pyrrolidone (PVP).

More particularly reagents for reducing the water activity include 1-10% (w/v) PEG with average molecular weight from 1.000 to 10.000 Da.

The reagents suited for reducing unspecific protein interactions include neutral, anionic, cationic and block-copolymer detergents or surfactants.

Particularly the surfactants are selected from the group consisting of Tween 20, Tween 40, the pluronics family, and NP40 detergents in concentrations below 2%.

pH stabilizing reagents include phosphate, citrate, borate buffers, in addition to Good buffers.

In particular, pH buffer systems based on phosphates, e.g. Tris, MES and Hepes, at pH 5-8 are preferred.

It should be clear that a suitable buffer may contain only one or multiple reagents with the above general properties.

In addition to the above described complex formation step, the purification process according to the invention requires additional steps. Even though the skilled person may not have considered the order of the steps before or even the application or combination of such additional step for purifying a target molecule, the steps as such are well known to the skilled person.

In a particular embodiment the target molecule is a bio-molecule. Bio-molecules comprise proteins, peptides, oligopeptides, lipoproteins, apolipoproteins, phospho proteins, glucoproteins, oligosaccharides, polysaccharides, lignin's, lipids including fatty acids, glycolipids, phospholipids and sterols, carbohydrates, nucleotides including deoxyribonucleic acid and ribonucleic acid, vitamins, whole cells and fractions thereof, and virus particles and fractions thereof.

Targets molecules further include synthetic molecules, organic synthesis precursors, products from organic synthesis, molecules from natural extracts and natural minerals including rare earth minerals.

Other targets of interest comprise specific isomers, for example enantiomers, from mixtures of stereoisomers arising from natural or synthetic sources.

In a more particular embodiment the bio-molecules include proteins suited for therapeutical use and manufactured in cells systems, and in particular antibodies.

A key step in the purification process of the invention is the separation of the TBP-target molecule complex from other components and reduction of the process liquid volume. Two methods are particularly relevant i) physical separation, or ii) binding of the complex to a support material.

Separation systems are widely used in pharmaceutical and chemical processing, food and beverage processing, and waste water treatment.

Physical separation of the complex can be done by, for example, simple gravitation sedimentation, batch centrifugation, ultracentrifugation using very high centrifugal force, continuous centrifugation, simple filtration, forced filtration or cross flow filtration in hollow fibre or membrane systems.

The complex of the innovation can be separated as solids, as wet slurries, as a paste or in the form of a complex enriched solution.

Centrifuges are particularly relevant for a separation process of the invention, as the unit operation is simple, easily scalable, robust, generally uses a small footprint, and can generally be operated continuously.

The optimum type of centrifuges depends on the specific sample volume, viscosity, density, complex size distribution, concentration and flow speed needed.

Batch centrifuges include designs with swinging-bucket, fixed-angle or vertical rotors. The centrifugation process can be arranged as simple differential centrifugation or more complex density gradient, isopycnic or rate zonal centrifugation which can separate on buoyancy and sedimentation speed.

Continuous centrifuges are well known, including solid bowl centrifuges or decanters and disk bowl centrifuges. The simplest form of continuous centrifuges consists of a bowl spinning about a vertical axis. Samples are introduced into this and under centrifugal force the heavier liquid or solids pass to the outermost regions of the bowl, whilst the lighter components move towards the centre. Collection pipes and internal conical plates are arranged to give efficient separation.

Other designs optimized for separating liquid and solids include centrifuges with telescoping bowl, and horizontal bowl with scroll discharge. The latter is designed to continuously discharge the accumulated and separated solids or slurry. Similar centrifuges like perforated basket centrifuges and imperforated basket centrifuges can operate almost continuously for collecting the solids or slurry.

Other relevant unit operations for separation of the TBP-target complex are sedimentation, flotation and filtration.

The complex can be separated by simple sedimentation or more preferably in a continuous sedimentation process.

In more detail, continuous sedimentation equipment for separation of solid particles from liquids by gravitational sedimentation is designed to provide sufficient time for the sedimentation to occur and to permit the overflow and the sediment to be removed without disturbing the separation. Continuous flow through the equipment is generally desired, various shaped vessels are used, with a sufficient cross-section to keep the velocities down and fitted with slow moving scrapers, conveyors and pumps to remove the settled solids.

Multiple designs of continuous thickeners are known, which balance the rate of sedimentation in a particular zone to the counter-flow velocity of rising fluids for separating or enriching solids or slurries.

Filtration instruments for separating and collecting mainly large quantities of solids in the form of a build-up filter cake include the plate and frame press and various rotary presses.

Instead of settling out solids or particles, these can be floated to the surface by the use of air bubbles. This technique is often referred to as flotation and depends upon the relative tendency of air and water to adhere to the particle surface. The water at the particle surface is displaced by air, after which the buoyancy of the air is sufficient to carry both the particle and the air bubble up through the liquid.

Centrifugal filters are convenient combinations of the above mentioned centrifuges combined with a suitable semi permeable filter. Other forced filtrations use pressurized liquids or vacuum to speed up the filtering process.

Filters and membranes can be used as efficient unit operations for separating the TBP-target complex of the invention. The filter or membrane is semi permeable and will retain the particles based on size and allow the liquids and smaller sized particles to pass. Some membranes will separate on other physical properties, including charge or hydrophilicitet.

Simple batch filtration is well known and the filter arranged in funnels and columns and accelerated by pressure and/or vacuum.

Cross flow, hollow fiber and similar dialysis systems are of special relevance for the separation of the complex of the invention. In these forced filtration processes the solids are continuously removed from the membrane surface to prevent fouling and build-up of a filter cake.

The membrane system can be a cylindric construction arranged in staked sheets or as bundled hollow fibres. In a particularly preferred arrangement, the cross flow or hollow fiber system is fed with the complex mixture and a buffer and used for removing contaminants, washing and concentrating the complex in a continuous mode.

It should be clear that the above mentioned unit operations are also preferable for collecting and washing TBP-target complex bound supports and for general concentration or change of buffers during the purification process.

Another important unit operation for the present invention is separating the TBP-target molecule complex by binding to a support. The support will typically be an insoluble solid or other vice easily collectable material with binding capability against one of the binding functionalities on the TBP.

Attractive binding pairs include those where the immobilized ligand is a small molecule and especially ligands which are easily available, synthetic or resistant to microbiological degradation. Examples include biotin which can easily be covalently coupled to many supports and are chemically robust.

In one embodiment isolation of the target from the complexes is obtained by first capturing the target-TBP complexes on a support, followed by elution and collection of the target molecule from the support.

The TBP-target molecule form complexes of medium binding affinity, and the complex binds non-covalently to a generic affinity matrix with a strong binding affinity. The target biomolecule is recovered by specific elution from the support, typically a generic matrix, leaving the TBP attached to the capturing ligand on the matrix, due to a tight binding to the ligand preventing leakage from the solid phase matrix.

The TBP acts as the linking partner between the support and the target molecule. In one particular embodiment the affinity of the TBP towards the immobilized ligand is stronger than the affinity towards the target molecule. This difference in binding affinity can be expressed as the ratio between the equilibrium dissociation constants. In one embodiment this ratio is at least 1 at standard conditions. More preferably binding of TBP to the target is weaker than binding of TBP to the ligand. This secures that the TBP stays attached to the solid phase during washing steps and elution of the target molecule. The above ratio between the equilibrium dissociation constants can be obtained by varying the respective equilibrium dissociation constants of the TBP accordingly. In one embodiment of the invention the TBP has an equilibrium dissociation constant towards a target molecule, $K_{D,t}$ in the range from $10^{-2}$ to $10^{-13}$ M, e.g. $10^{-8}$ M, and an equilibrium dissociation constant towards a catching ligand, $K_{D,s}$ in the range from $10^{-9}$ to $10^{-16}$ M, e.g. $10^{-10}$ M, and at the same time the ratio, $K_{D,t}/K_{D,s}$, should be matched such that the ratio is at least $10^0$, more particularly at least $10^1$, more particularly $10^2$, more particularly $10^3$ and even more particularly $10^4$.

Particularly the said TBP has an equilibrium dissociation constant, $K_{D,t}$ towards the target molecule in the range from $10^{-4}$ to $10^{-13}$ M, more particularly in the range from $10^{-6}$ to $10^{-13}$ M, and an equilibrium dissociation constant, $K_{D,s}$ towards the catching ligand in the range from $10^{-9}$ to $10^{-16}$ M, more particularly in the range from $10^{-11}$ to $10^{-16}$ M.

In general the binding towards the ligand or the column should be as strong as possible. Therefore the value at the upper end of the range is not important in respect of $K_{D,s}$ In the context of the present invention the equilibrium dissociation constant are measured according to the reaction:

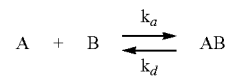

A and B represents the binding partners: the target molecule and the TBP or alternatively the TBP and the catching ligand immobilized on the solid phase matrix.

The rate constants for the reaction above represent the rate at which the two molecules A and B associates and dissociates $$\text{Dissociation rate} - \frac{d[AB]}{dt} = k_d[AB]$$

-continued $$\text{Association rate: } \frac{d[AB]}{dt} = k_a[A][B]$$

When the rates are equal at equilibrium $k_a[A][B]=k_d[AB]$, which gives $$\frac{k_d}{k_a} = \frac{[A][B]}{[AB]} = K_D$$

$$\frac{k_a}{k_d} = \frac{[AB]}{[A][B]} = K_A$$

The candidate binding domains to be employed in the TBP should be evaluated according to the apparent equilibrium dissociation constants based on the total binding affinity of each of the binding functionalities in a given TBP molecule irrespective of whether it contains one or several binding sites for each specificity (target/capturing ligand). If e.g. A and B represent protein A (has four to five binding domains) and avidin (having four binding sites) respectively the above ranges should apply for one protein A molecule fused to one avidin molecule. However, this does not exclude the possibility that e.g. the TBP molecule could be composed of several binding sites for the target and several binding sites for the ligand on the matrix. The TBP could e.g. in another embodiment consist of 3 protein A molecules linked to one or more avidin molecules. Therefore the specified ranges as defined above should in the context of the present invention be evaluated based on the apparent binding constants for the binding domains in common.

In the context of the present invention the specified equilibrium dissociation constants can be determined by surface plasmon resonance (SPR) technology using a Biacore Instrument. As a suitable starting point for selecting different binding domains to be combined in the TBP molecule published $K_D$'s may be used.

The two binding pairs, referred to in the present application as a first and a second binding functionality, should be selected based on the $K_D$'s during specific binding conditions, but also considering the planned elution conditions, when the target is recovered and the TBP molecule remains on the support.

As described above determination of dissociation affinities of various binding domains in the context of a TBP molecule is accomplished by using surface plasmon resonance (SPR). Such evaluation can be done with the Biacore system. Biacore has commercial instrumentation where measurements based on SPR make determinations on protein-protein interactions. The evaluation was conducted having a TBP or a target molecule immobilized on the sensor chip used in the Biacore instrument. The Biacore system defines the characteristics of proteins in terms of their specificity of interaction with other molecules, the rates at which they interact (association and dissociation), and their affinity (how tightly they bind to another molecule). This technique has been described e.g. for determining the binding interactions between specific antibodies and their target (see e.g. Rönnmark, 2002, Eur. J. Biochem., 269: 2647-2655).

Quantitative measurement of non-covalent protein-ligand interactions is well known. The methods suited for quantitative measurement of binding constants of particular relevance for the present invention include various versions of surface plasmon resonance (SPR) and circular dichroism (CD).

Other methods include mass spectrometry methods for dynamic titrations like ESI-MS titration, HPLC-ESI-MS titration or MALDI-SUPREX titration.

Other methods are based on determining the dissociation constant of a ligand at a binding site indirectly by competitive displacement of a radioactive ligand or by measurement of NMR chemical shift as function of concentration, fluorescence spectroscopy analysis of e.g. signal quenching, X-ray crystallographic measurement of the ligand occupancy, isothermal calorimetry (ITC) or enzyme inhibition.

Yet other methods use labeled ligands, for example capillary electrophoresis with laser-induced fluorescence detection of enzyme labeled ligands.

Alternatively, binding constants can be found from computational techniques by using de novo design, data mining and sophisticated algorithms.

In the context of the present invention the appropriate ranges for the equilibrium dissociation constants should apply to the complete TBP and not to the individual binding parts measured separately.

Moreover, if a single candidate binding domain has a weaker binding affinity towards the target or ligand than required according to the present invention, it still could be applicable by combining several such candidate binding domains into one TBP.

This is due to the valence effect. It is possible to obtain an increased binding strength due to an avidity gain. Single domains with a low intrinsic affinity combined into multimers often generates avidity effects which lead to slower dissociation rates and increased functional affinities by more than 100 fold (MacKenzie, C. R. et al (1996), Analysis by surface plasmon resonance of the influence of valence on the ligand binding affinities and kinetics of and anti carbohydrate antibody. Journal of Biological Chemistry, 271, 1527-1533). It is possible to measure effects from monovalent and bivalent bindings, but at higher binding valences the situation becomes so complex that it is difficult to distinguish between different binding valances. Nevertheless relative data can be obtained and are used in the context of the present invention Due to the described differences in equilibrium dissociation constants the target molecule can be efficiently eluted without eluting the TBP. Elution can in one embodiment be performed by changing either pH, ionic strength or chaotropic ions in solution, or any combination thereof.

The $K_D$ value can be influenced by changing conditions like pH, ionic strength, temperature and polar properties. Unfortunately, the literature values for $K_D$ are not always listed at relevant elution conditions. The skilled in the art will be able to find elution conditions which will only break the weakest binding without disturbing the stronger binding in cases were the binding to the solid matrix is sufficiently strong (i.e. $K_{D,s}<10^{-9}$ M and the ratio between $K_D$ values is at least 1 when measured at standard binding conditions) The criteria for selecting the target specific binding pairs of the invention resemble those for the traditional affinity chromatography with regard to dissociation constant, specificity, binding and possible elution conditions. However, since elution conditions are usually different from the conditions applied when measuring $K_D$'s on the Biacore instrument in the present invention the limits set for the applicable ranges of the two distinct binding affinities of the TBP has been determined under standard conditions.

The criteria for selecting the specific ligand binding domains of the invention are somewhat different from the criteria used in the traditional affinity chromatography, as the TBP molecule is not to be eluted from the support.

Binding domains which are specific and strong, but cannot be broken under normal elution conditions are not suited for traditional affinity chromatography. Such binding domains can be used in the present invention. Examples include the very specific biotin-Streptavidin binding, which for most practical applications cannot be reversed under elution conditions and consequently is well suited as one of the binding pairs of the invention.

In general, the binding between TBP and the ligand should be stronger than the binding between TBP and the target and strong enough to prevent leakage of the TBP molecule from the support during elution of the target.

Preferred ligand-TBP binding pairs are strong and exhibit no or little reduction in binding strength due to changing pH, ionic strength, solvents, chaotropic agents, temperature etc.

In one embodiment the TBP is a fusion polypeptide. Such fusion polypeptides can either be prepared by chemically linking two appropriate proteins or alternatively in another embodiment the fusion protein can be produced as a recombinant polypeptide. The fusion polypeptide can be linked in any suitable way e.g. by a linker segment. and the fusion polypeptide should at least comprise the binding domains of the selected proteins. The linker peptide should be selected in such a way that it is not unstable resulting in degradation. The linker could e.g. be a highly O-glycosylated linker as linkers between catalytic domains and carbohydrate binding domains known from fungal carbohydrases, or it could be proline rich linkers.

In another embodiment the TBP is composed of fragments. Such fragment can e.g. be covalently coupled by site specific and/or enzyme catalyzed peptide ligation or oligomerization techniques.

The TBP comprises at least one first binding functionality capable of binding to the target molecule with the desired binding specificity as described. The first binding functionality can be comprised in the complete protein or it can be a fragment of the protein which has retained its binding specificity. Many proteins have been described in the literature displaying affinity towards biomolecules, e.g. peptides, proteins, DNA, RNA, carbohydrates, and all such proteins or fragments thereof are potentially useful in the context of the present invention as candidates for the TBP.

The said first binding functionality directed towards the target molecule can in one embodiment therefore be selected from but not limited to the group consisting of protein A, protein A fragments, protein A derived domains (e.g. domains known as an Affibody®), antibodies, antibody fragments, lipocalins, and lectins.

Combinatorial protein engineering has been applied to develop artificial proteins that can bind to selected targets with high affinity and be used as alternatives to antibodies (Nygren, P.-Å. & Skerra, A. (2004). Binding proteins from alternative scaffolds. J. Immunol. Methods, 290, p. 3-28; Binz, H. K. & Plückthun, A. (2005). Engineered proteins as specific binding reagents. Curr. Opin. Biotech. 16, p. 459-469). In the context of the present invention the term "affibody" defines a class of engineered proteins selected for their specific binding activity towards a desired target and based on the Z domain, which is a 58 residue three-helical bundle derived by a single amino acid substitution in the B domain of staphylococcal protein A (SPA)(Nilsson, B., Moks, T., Jansson, B., Abrahmsén, L., Elmblad, A., Holmgren, E. et al. (1987) Protein Eng. 1, p. 107-113). The Z domain binds to the Fc region of immunoglobulins as do the five homologous SPA domains, but unlike the parental domain it does not bind to the Fab region. Such affibodies are examples of a protein A derived binding domain.

The TBP also comprises at least one second binding functionality capable of binding to the catching ligand immobilized on the (solid) support. This second binding functionality can be comprised in the complete protein or it can be a fragment of the protein which has retained its binding specificity. In one embodiment the second binding functionality is selected from but not limited to the group consisting of avidin, streptavidin, neutravidin, steroid receptor, antibody, antibody fragment, amyloglucosidase (AMG), enzyme domain (e.g. cellulose binding domain, CBD), lipocalins, and lectins. As stated above these candidates, for the second binding functionality, are meant as examples illustrating the invention, however, these examples should not be seen as the only usable combinations.

In one embodiment the antibody is selected from the group consisting of Llama and camel antibodies.

In a particular embodiment the TBP according to the invention comprises at least one binding domain of protein A fused to at least one biotin binding domain of avidin, streptavidin or neutravidin.

In a particular embodiment the TBP according to the invention comprises at least one binding domain of a protein A derived binding domain fused to at least one biotin binding domain of avidin, streptavidin or neutravidin.

In another particular embodiment the TBP comprises at least one binding domain of an affibody fused to at least one biotin binding domain of avidin, streptavidin or neutravidin.

In another particular embodiment the TBP comprises at least one binding domain of an antibody fused to at least one biotin binding domain of avidin, streptavidin or neutravidin.

In another particular embodiment the TBP comprises at least one binding domain of protein A fused to AMG, CBD or (VhhRR6(R2)) (VhhRR6(R2)) indicate the variable region from a Llama single chain antibody reacting against the hapten azo-dye Reactive Red (RR6) (Frenken et al. J. Biotechnology 78 (2000) 11-21).

In another particular embodiment the TBP comprises at least one binding domain of a protein A derived binding domain fused to AMG, CBD or (VhhRR6(R2)).

In another particular embodiment the TBP comprises at least one binding domain of an affibody fused to AMG, CBD or (VhhRR6(R2)).

In another particular embodiment the TBP comprises at least one binding domain of an antibody fused to AMG, CBD or (VhhRR6(R2)).

The TBP can as illustrated in the examples be linked chemically; however, a more cost efficient way to produce the TBP would be to express it as a recombinant fusion protein.

In one embodiment of the invention, the fusion polypeptide is produced as a recombinant polypeptide.

In a particular embodiment the fusion protein is expressed as a recombinant protein, particularly the fusion protein is in one embodiment recombinant Streptavidin linked to protein A. Such fusion protein can be produced intracellular in *E. coli* as described in Sano (T. Sano and C. R. Cantor (1991) BioTechnology 9 p 1378-1381), preferentially using the construct pTSAPA-2 carrying two IgG binding domains. However this construct is not industrially feasible as intracellular production with recovery of inclusion bodies in *E. coli* do not give industrially relevant yields and the production process is highly complex. A process based on a secreted fusion protein produced in e.g. *Bacillus* or *Aspergillus* is of much higher industrial relevance.

The nucleotide sequence encoding the fusion protein may preferably be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors preferably contain one or more selectable markers which permit easy selection of transformed cells. A selectable marker is a gene the product of which provides for biocide or viral resistance, resistance to heavy metals, prototrophy to auxotrophs, and the like.

A conditionally essential gene may function as a non-antibiotic selectable marker. Non-limiting examples of bacterial conditionally essential non-antibiotic selectable markers are the dal genes from *Bacillus subtilis, Bacillus licheniformis*, or other *Bacilli*, that are only essential when the bacterium is cultivated in the absence of D-alanine. Also the genes encoding enzymes involved in the turnover of UDP-galactose can function as conditionally essential markers in a cell when the cell is grown in the presence of galactose or grown in a medium which gives rise to the presence of galactose. Non-limiting examples of such genes are those from *B. subtilis* or *B. licheniformis* encoding UTP-dependent phosphorylase (EC 2.7.7.10), UDP-glucose-dependent uridylyltransferase (EC 2.7.7.12), or UDP-galactose epimerase (EC 5.1.3.2). Also a xylose isomerase gene such as xylA, of *Bacilli* can be used as selectable markers in cells grown in minimal medium with xylose as sole carbon source. The genes necessary for utilizing gluconate, gntK, and gntP can also be used as selectable markers in cells grown in minimal medium with gluconate as sole carbon source. Other examples of conditionally essential genes are known in the art. Antibiotic selectable markers confer antibiotic resistance to such antibiotics as ampicillin, kanamycin, chloramphenicol, erythromycin, tetracycline, neomycin, hygromycin or methotrexate.

Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity with the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication which functions in a cell. The term "origin of replication" or "plasmid replicator" is defined herein as a nucleotide sequence that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98:61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a polynucleotide encoding the TBP of the present invention may be inserted into the host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Recombinant host cells, comprising a polynucleotide encoding the TBP of the present invention, are advantageously used in the recombinant production of the polypeptides. A vector comprising a polynucleotide encoding the TPB of the present invention is introduced into a host cell so that the vector is maintained as a chromosomal integrant or as a self-replicating extrachromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote.

Useful unicellular microorganisms are bacterial cells such as gram positive bacteria including, but not limited to, a *Bacillus* cell, e.g., *Bacillus alkalophilus*, *Bacillus amyloliquefaciens*, *Bacillus brevis*, *Bacillus circulans*, *Bacillus clausii*, *Bacillus coagulans*, *Bacillus lautus*, *Bacillus lentus*, *Bacillus licheniformis*, *Bacillus megaterium*, *Bacillus stearothermophilus*, *Bacillus subtilis*, and *Bacillus thuringiensis*; or a *Streptomyces* cell, e.g., *Streptomyces lividans* and *Streptomyces murinus*, or gram negative bacteria such as *E. coli* and *Pseudomonas* sp. In a preferred aspect, the bacterial host cell is a *Bacillus lentus*, *Bacillus licheniformis*, *Bacillus stearothermophilus*, or *Bacillus subtilis* cell. In another preferred aspect, the *Bacillus* cell is an alkalophilic *Bacillus*.

The introduction of a vector into a bacterial host cell may, for instance, be effected by protoplast transformation (see, e.g., Chang and Cohen, 1979, *Molecular General Genetics* 168: 111-115), using competent cells (see, e.g., Young and Spizizin, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278).

The host cell may also be a eukaryote, such as a mammalian, insect, plant, or fungal cell.

In a preferred aspect, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

In an even more preferred aspect, the yeast host cell is a *Candida*, *Hansenula*, *Kluyveromyces*, *Pichia*, *Saccharomyces*, *Schizosaccharomyces*, or *Yarrowia* cell.

In a most preferred aspect, the yeast host cell is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis* or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium*, *Aspergillus*, *Aureobasidium*, *Bjerkandera*, *Ceriporiopsis*, *Coprinus*, *Coriolus*, *Cryptococcus*, *Filobasidium*, *Fusarium*, *Humicola*, *Magnaporthe*, *Mucor*, *Myceliophthora*, *Neocallimastix*, *Neurospora*, *Paecilomyces*, *Penicillium*, *Phanerochaete*, *Phlebia*, *Piromyces*, *Pleurotus*, *Schizophyllum*, *Talaromyces*, *Thermoascus*, *Thielavia*, *Tolypocladium*, *Trametes*, or *Trichoderma* cell.

In a most preferred aspect, the filamentous fungal host cell is an *Aspergillus awamori*, *Aspergillus fumigatus*, *Aspergillus foetidus*, *Aspergillus japonicus*, *Aspergillus nidulans*, *Aspergillus niger* or *Aspergillus oryzae* cell. In another most preferred aspect, the filamentous fungal host cell is a *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, or *Fusarium venenatum* cell. In another most preferred aspect, the filamentous fungal host cell is a *Bjerkandera adusta*, *Ceriporiopsis aneirina*, *Ceriporiopsis aneirina*, *Ceriporiopsis caregiea*, *Ceriporiopsis gilvescens*, *Ceriporiopsis pannocinta*, *Ceriporiopsis rivulosa*, *Ceriporiopsis subrufa*, or *Ceriporiopsis subvermispora*, *Coprinus cinereus*, *Coriolus hirsutus*, *Humicola insolens*, *Humicola lanuginosa*, *Mucor miehei*, *Myceliophthora thermophila*, *Neurospora crassa*, *Penicillium purpurogenum*, *Phanerochaete chrysosporium*, *Phlebia radiata*, *Pleurotus eryngii*, *Thielavia terrestris*, *Trametes villosa*, *Trametes versicolor*, *Trichoderma harzianum*, *Trichoderma koningii*, *Trichoderma longibrachiatum*, *Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology*, *Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

The catching ligand according to the invention is covalently attached to the support. As explained above the ligand according to the present invention is different from the ligand used in traditional affinity chromatography where the purpose of the ligand is to bind the target. In the present invention the ligand should bind to the TBP. Ligands are well known in the art and below are given examples that can be applied according to the invention. In the context of the present invention in one particular embodiment instead of a ligand attached to the solid phase the solid phase could alternatively comprise a binding affinity or binding site towards the TBP. An example could be cellulose as the solid phase and CBD (cellulose binding domain) as part of the TBP.

The ligand (e.g. biotin or similar specific molecules of low molecular weight (LMW)) is then covalently attached to this material. Several coupling chemistries of ligand molecules to the solid support can be selected from text books on the subject (Protein Purifuication, 1998, 2ed, eds. Janson, J-C., Rydén, L, Wiley & sons inc. New York). Based on the particular purification task the best candidate of ligand derivatives is coupled to the best choice of solid support, e.g. solid phase matrix or particles. Production process properties of the affinity solid matrix are analyzed through practical laboratory and pilot testing.

The ligands may be attached to the solid phase material by any type of covalent bond known per se to be applicable for this purpose, either by a direct chemical reaction between the ligand and the solid phase material or by a preceding activation of the solid phase material or of the ligand with a suitable reagent known per se making it possible to link the matrix backbone and the ligand. Examples of such suitable activating reagents are epichlorohydrin, epibromohydrin, allyl glycidylether; bis-epoxides such as butanedioldiglycidylether; halogen-substituted aliphatic compounds such as di-chloro-propanol, divinyl sulfone; carbonyldiimidazole; aldehydes such as glutaric dialdehyde; quinones; cyanogen bromide; periodates such as sodium-meta-periodate; carbodiimides; chloro-triazines such as cyanuric chloride; sulfonyl chlorides such as tosyl chlorides and tresyl chlorides; N-hydroxy succinimides; 2-fluoro-1-methylpyridinium toluene-4-sulfonates; oxazolones; maleimides; pyridyl disulfides; and hydrazides. Among these, the activating reagents leaving a spacer group SP1 different from a single bond, e.g. epichlorohydrin, epibromohydrin, allyl-glycidylether; bis-epoxides; halogen-substituted aliphatic compounds; divinyl sulfone; aldehydes; quinones; cyanogen bromide; chloro-triazines; oxazolones; maleimides; pyridyl disulfides; and hydrazides, are preferred.

In one embodiment the ligand is chosen from but not limited to the group consisting of biotin, acarbose, steroids, haptens, epitope-peptides, dyes and enzyme inhibitors. In a particular embodiment the ligand is biotin. The ligand can be chemically attached to the support. In a particular aspect the support is a solid support. The preferred supports are robust and cheap. The material can be the same as used in traditional affinity chromatography, or materials used in ion exchange, hydrophilic interaction chromatography, and water filtration or similar. Preferably, the support with immobilized ligands is not susceptible to chemical changes or microbial activity during storage or use.

The support can be in the form of distinctly separated particles, beads or in the form of sheets, membranes, pins, mesh or other three dimensional constructs. The support can be functionalized mainly on the surface or throughout the material. The support can be a rigid solid, semi rigid or a soft gel.

Preferable support materials include Sartobind Membrane Adsorbers and SartoAlMs membranes (Sartorius Stedim), polystyrene latex micro particles and Sepharose and Superose beads (GE Healthcare).

It should be understood that the support can be packed as beads in columns, as sheets or membranes arranged in cylindrical or stacked constructions or free floating in a liquid.

The latter support being collected and washed with unit operations like sedimentation, centrifugation, filtration, cross filtration or hollow fibers as described above.

Other support materials comprise any natural or synthetic and organic or inorganic material known per se to be applicable in solid phase separation of proteins and other biomolecules, e.g. natural or synthetic polysaccharides such as agar-agar and agaroses; celluloses, cellulose ethers such as hydroxypropyl cellulose, carboxymethyl celluose; starches; gums such as guar gum, and gum arabic, gum ghatti, gum tragacanth, locust bean gum, xanthan gum; pectins; mucins; dextrans; chitins; chitosans; alginates; carrageenans; heparins; gelatins; synthetic polymers such as polyamides such as polyacrylamides and polymethacrylamides; polyimides; polyesters; polyethers; polymeric vinyl compounds such as polyvinylalcohols and polystyrenes; polyalkenes; inorganic materials such as silicious materials such as silicon dioxide including amorphous silica and quartz; silicas; metal silicates, controlled pore glasses and ceramics; metal oxides and sulfides, or combinations of these natural or synthetic and organic or inorganic materials. The matrix backbone is preferably selected from agar-agar, agaroses, celluloses, cellulose ethers such as hydroxypropyl cellulose, carboxymethyl cellulose, polyamides such as poly (meth)acrylamides, polyvinylalcohols, silicas, and controlled pore glasses.

Particular solid phase materials as matrix backbones are e.g. agar or agarose beads such as Sepharose and Superose beads from GE Healthcare, and Biogel A from Biorad; dextran based beads such as Sephadex, GE Healthcare; cellulose based beads and membranes such as Perloza cellulose from Lontosorb; composite beads such as Sephacryl and Superdex, GE Healthcare; beads of synthetic organic polymers such as Fractogel from Tosoh Lifesciences LLC; POROS media from Applied Biosystems, Bio-Rex, Bio-Gel P and Macro Prep from Biorad, HEMA and Separon from TESSEK and Hyper D and Trisacryl media from Pall Corporation, Enzacryl and Azlactone, 3M; beads of siliceous materials such as controlled pore glass, PROSEP, from Millipore, and Spherocil, Pall Corporation; and coated silica composites in the form of beads or membranes such as ACTI-DISK, ACTI-MOD and CycloSep from Arbor Technologies.

Yet another type of unit operations of relevance for the separation of the TBP-target molecule complex, washing or collecting the target molecule comprise liquid extraction processes.

The liquid extraction processes or solvent extraction utilizes the components relative solubility and preference for different immiscible liquid phases. By separating the phases, the separation of component's can be facilitated in an efficient way in industrial scale.

Of particular relevance for the present invention aqueous two phase systems using mixtures of polymers, kosmotropic or chaotropic salts are included.

PEG-Dextran, PEG-sodiumcarbonate, PEG and phosphates, citrates or sulfates and various hydroxypropyl starch, starch, agar or gelatine based aqueous systems are known for extraction of labile biomolecules. Preferable aqueous two phase systems comprise 10-15% solutions of PEG, phosphate and sodium chloride at pH 6.

Other preferable liquid extraction methods use so-called critical phase or super critical phase extraction using gasses or liquids above a critical point where they can behave as organic solvents. Water and carbon dioxide are the most commonly used supercritical fluids The formation of the complex between target molecule and TBP in solution prior to separation steps allows for several attractive downstream purification workflows.

The workflow can consist of several general unit operations, i.e. i) formation of complex in solution according to the invention, ii) one or several separation steps, iii) a process step where the complex between target molecule and TBP is dissolved, iv) an operation where the TBP is removed and v) a step where the target is collected. It should be understood that the order and number of individual steps and unit operations can be varied.

The workflows can be designed with a TBP capturing step before or after dissolution of the complex. Also, the workflows can make use of specific TBP binding beads or other supports in free suspension, floating, fluidized or packed in columns.

Not limiting examples of combinations of unit operations or workflows include:
1. Incubation of target molecule and TBP in bulk solution with or without added enhancement buffer
2. Transfer to column packed with TBP binding support
3. Wash of column with TBP-Target complex bound support
4. Elution of target using, for example, a low pH buffer
5. Collection of target
6. Change of buffer in target solution Another workflow sequence using TBP binding support in the form of beads
1. Incubation of target and TBP in bulk solution with added enhancement buffer
2. Addition of beads with TBP specific binding capability
3. Wash of beads in centrifuge or membrane filtration system
4. Elution of beads at low pH
5. Removal of beads by centrifugation or sedimentation
6. Change of buffer in target solution
7. Collection of target Another workflow sequence using isolated complex, followed by dissolving complex and removal of TBP with a support material:
1. Incubation of target and TBP in bulk solution with added precipitation enhancement buffer
2. Centrifugation and isolation of TBP-Target complex
3. Dissolution of precipitated complexes in low pH buffer
4. Pass of solution through TBP binding membrane to remove TBP
5. Change of buffer in target solution
6. Collection of target Yet a workflow sequence using a general and a target specific precipitation step:
1. Treatment of target solution under general salting out conditions
2. Centrifugation to collect precipitates
3. Dissolution of precipitated proteins in appropriate low salt buffer
4. Incubation of target and TBP in bulk solution with added precipitation enhancement buffer
5. Centrifugation and isolation of TBP-Target complex
6. Dissolution of precipitated complexes in low pH buffer
7. Pass of solution through TBP binding membrane to remove TBP
8. Change of buffer in target solution
9. Collection of target It should be understood that the sequence of formation of complex, isolation, dissolution of the complex and removal of TBP can be repeated. Also, that different precipitation enhancer buffers can be used in repeated steps and concentration steps can be included.

The TBP-Target complex of the invention allows for a truly continuous down stream purification workflow, as the target molecule can be collected in a continuous process. A not limiting example of combinations of unit operations or workflows include
1. Mixing of target and TBP in a continuous stream
2. Continuously separation of TBP-Target complex
3. Dissolution of complex by adding a low pH buffer
4. Capturering of TBP by adding beads
5. Continuous separation of beads with TBP
6. Collection of target In more detail, for example
1. TBP, target and buffer is mixed in a continuous stream and fed to a continuous centrifuge
2. The complex is continuously separated in a stream, and the other stream discarded
3. The stream containing the TBP-Target molecule complex is added a low pH buffer to separate target bio molecule and TBP, before being
4. Added microparticles with a TBP specific ligand for capturing the TBP molecule
5. The microparticles are separated in a stream using a continuous centrifuge or sedimentation
6. The target containing stream is concentrated and the buffer changed in a continuous hollow fibre system, before
7. The target stream is collected and further processed in polishing steps In the above outlined unit operations the target has to be collected. This operation requires dissolving or eluting the complex of the invention, which in the context of the present invention is to be understood as treating the complex under conditions in such a way that TBP and target molecules will predominately separate from each other. The conditions should leave the target molecule unaltered and intact.

This can be done by conditions well known to the skilled artist. Numerous ready-to-use elution reagents are commercially available and protocols are accessible in the public domain. The possible favourable dissolving or elution conditions comprise of changing the pH, the salt content, the temperature or inducing shear stress to the complex. Also, the condition can comprise of changing the equilibrium conditions by adding competing amounts of binding components.

It should be understood that it is preferred that the dissolving or elution conditions will leave the binding functionalities on the TBP towards support unaltered. The choice of conditions depends on the nature of the TBP-to-target binding.

For example, preferred conditions for reversing protein A to immunoglobulin binding include using a glycin buffer at pH 2-4, a citrate buffer at pH 3-4, chaotropic salts, metal complexing reagents, special neutral buffers like Gentle Ag/Ab Binding Buffer (Thermo scientific Product #21012) or adding small molecules mimicking the binding pattern of the target immunoglobulin to compete out the TBP.

The purification process according to the invention as described in detail above may be utilized in a kit based on the said process.

In a further aspect the invention therefore relates to a kit for optimization of complex formation comprising a suitable TBP and support material for removing the TBP.

Preferred kits for purification of a specific target molecule include i) the target binding protein (TBP) supplied in a concentrated solution, ii) concentrated buffer mixtures suited for the complex formation and the dissolution of the target and the TBP complex, respectively, iii) support material for removing TBP, and iv) instructional guidelines.

A kit may further contain components and instructional guidelines for optimizing the TBP concentration using a turbidimetry, nephelometry or similar assay, and optionally computer software and algorithms. Further components could e.g. include appropriate standards.

All the reagents, buffers and support materials are preferably provided as sterile solutions.

Such kits may also conveniently be used for screening a library comprising one or more clones expressing TBPs against a target of interest. In one additional aspect the invention therefore relates to a method for selecting a TBP suitable for complex formation with a target polypeptide of interest comprising: (a) contacting individual TBPs obtainable from a library of TBPs with the target of interest, and (b) determining complex formation.

The above screening method in a further embodiment comprises adding a complex enhancing buffer and/or changing the ratio of target to TBP in step (a).

EXAMPLES

Example 1. SPDP-SMCC Chemo Selective Protein Conjugation Procedure

The example describes the chemo selective conjugation method used for the preparation of ProteinA-Avidin conjugates.

ProteinA was activated with N-succinimidyl 3-(2-pyridyldithio) propionate (SPDP), followed by Dithiothreitol (DTT) reduction to give free thiols, which was reacted with Succinimidyl-4-(N-maleimidomethyl)cyclohexane-1-carboxylate (SMCC) activated Avidin.

All incubations was done on a temperature controlled water bath at 30° C. and the mixtures stirred with a miniature magnetic bar in seal polypropylene reaction tubes. The PD MidiTrap (GE Healthcare) columns were all equilibrated according to the product instruction prior to use.

Two reaction buffers were prepared: Buffer 1: 50 mM HEPES (Applichem, cat. no. A1069), 100 mM NaCl (Merck, cat. no. 1.06404), 2 mM EDTA, pH 7.0 and buffer 2: 50 mM MES (Sigma, cat. no. M2933), 100 mM NaCl, 2 mM EDTA, pH 6.0.

The freshly prepared mixtures of SPDP, SMCC, DTT, N-ethyl-maleimide (NEM) and cystein were kept on an ice bath prior to use:

Avidin and ProteinA Preparation:
Avidin (Sigma, cat. no. A9275) and ProteinA (GE Healthcare, cat. no 17-0872-50) was dissolved in buffer #1 (approx 28 and 24 mg/ml, respectively, 1.00 ml) desalted using a PD MidiTrap column (GE Healthcare). The proteins was eluted with buffer 1 (1.5 ml) and collected. The concentration was measured by UV (Abs280, 1 cm) 1.54, 62400 g/mol and (Abs280, 1 cm) 0.149, 42000 g/mol, respectively) and the concentration adjusted to 15.0 mg/ml and 12.5 mg/ml with buffer 1, respectively.

Avidin Activation with SMCC:
With high precision, SMCC (Sigma cat no M5525) was dissolved in dry NMP (Sigma-Aldrich cat. no. 494496, approx. 1.00 ml, 16.00, 8.00, or 4.00 mg/ml)

The SMCC solution (0.050 ml) was quickly added the Avidin solution. The stirred reaction mixture (Avidin:SMCC 1:10; 1:5, and 1:2.5 respectively) was incubated at 30° C. for 30 minutes.

The reaction mixture (1.00 ml) was loaded onto a PD MidiTrap column and the maleimid modified Avidin eluted with buffer 2 (1.5 ml), collected (10 mg Avidin/ml) and used for the ProteinA-Avidin interconjugation.

ProteinA Activation with SPDP:
With high precision, SPDP (Sigma, cat. no. P3415) was dissolved in dry NMP (approx. 1.00 ml, 18.8, 9.4 or 4.7 mg/ml)

The SPDP solution (0.050 ml) was added the ProteinA solution. The stirred reaction mixture (10 mg Avidin/ml, ProteinA:SPDP 1:10; 1:5, and 1:2.5 respectively) was incubated at 30° C. in a water bath for 30 minutes.

A sample (0.30 ml) was taken out for analysis of degree of substitution and stored cold, the rest of the mixture was immediately deprotected with DTT.

Deprotection of Thiol Modified ProteinA:
A DTT solution (Fluke, cat. no. 43819, 1 ml, 84 mg/ml in Buffer 1) was freshly prepared, and 0.050 ml added to 1.00 ml of the SPDP modified ProteinA solution and incubated on a water bath for 15 minutes.

The mixture (1.00 ml) was loaded onto a PD MidiTrap column, and the thiol modified ProteinA eluted with buffer 2 (1.5 ml), collected (6.35 mg ProteinA/ml) and used immediately for the ProteinA-Avidin interconjugation.

Inter Conjugation:
The Maleimid activated Avidin was mixed with buffer 1 and thiol functionalized Protein A, resulting in a total of 1.485 ml with 2.0 mg Protein A/ml and 3.0, 6.0, or 9.0 mg Avidin/ml (1:1, 1:2 or 1:3 in molar ratio, respectively).

The protein conjugation reaction mixtures, in total 1.485 ml, were allowed to incubate for 15, 30 or 120 minutes, respectively.

A further variation in the protein inter conjugation included a 66% and 33% dilution of the reagents with buffer 2, resulting in 1.33 and 0.66 mg Protein A/ml and 2.0 or 4.0, Avidin/ml and 1.0 or 2.0 mg Avidin/ml (1:1 or 1:2 in molar ratio and with 66% and 33% reduction in protein concentration, respectively). These protein conjugation reaction mixtures were allowed to incubate for 30 minutes.

Analysis of SPDP Substitution:
An ethanol amine solution (1 ml, 10% in Buffer 1) was prepared. Ethanolamine solution (0.025 ml) was added to the sample (0.300 ml) of the SPDP modified ProteinA solution.

The solution (0.250 ml) was loaded onto a PD5 column and SPDP modified ProteinA solution eluted with buffer 2 (0.750 ml) and collected. The solution was divided on two equal portions (0.300 ml) and DTT solution (0.030 ml, 100 mM, 15.4 mg/ml in Buffer 2) or buffer 2 (0.030 ml) was added, respectively.

Both solutions were measured at 343 nm (absorbtion) and the degree of SPDP substitution per ProteinA was calculated using the molar extension coefficient of 8000 for the 2-pyridinethione group. The results are summarized in FIG. 1.

Reactions Stop:
The conjugation process was stopped by the addition of NEM and cystein;

An N-ethyl Maleimid (NEM, Sigma, cat. no E1271, 1.0 ml, 20 mg/ml in buffer 2) and Cystein solution (Fluka cat. no 30150, 1.0 ml, 40 mg/ml in buffer 2), was freshly prepared.

NEM solution (0.075 ml per ml reaction solution) was added the conjugation reaction mixture, incubated for 15 min before being added cystein solution (0.075 ml per ml reaction solution). The resulting conjugates were stored at 5° C. before purification by gel filtration.

Numerous conjugates were prepared with variations of the SMCC and SPDP activation, ProteinA to Avidin ratio, inter conjugation time and inter conjugation concentration.

Large Scale Conjugation Procedure.

The example describes preparation of conjugates in larger scale.

A number of conjugates were prepared according to the general procedure described above, substituting the PD Meditrap columns with PD10 columns for desalting (2.50 ml sample and stacking buffer and 3.50 ml elution volume). The concentrations, ratios, reaction time and temperature were all the same. The final inter conjugation volume was up to three times that of example 1.

FIG. 1 is a table summarizing the prepared conjugates with respect to concentrations, stoichiometry and reaction time.

TBP Conjugate Purification:

The crude TBP conjugates was analyzed by gel filtration on a Superdex 200 HR 10/30 column (GE Healthcare, 30 cm×0.8 cm², column volume 24 ml, flow rate 0.40 ml/min) using a Hepes buffer (50 mM HEPES, 150 mM NaCl, pH 7.0). Samples of 100 ul were injected and the absorbance at 280 nm was recorded.

The Superdex 200 HR column was calibrated using molecular weight standards.

The prepared conjugates all gave three peaks, assigned to the conjugate population, a mixture of various homopolymers and small conjugates and unbound protein, respectively. The Protein A was barely visible due to the low extension coefficient. ($A_{280}$=0.149)

Larger scale conjugate preparative purifications were done on either a Superdex 200 or Superdex 75 using the same buffer as above (both columns, GE Healthcare, 60 cm×1.6 cm², column volume 120 ml), flow rate 1.00 ml/min). Samples of 2.0 ml were injected and the absorbance at 280 nm was monitored. Fractions of 1.00 ml were collected.

Conjugate 4, 5 and 11 was purified on Superdex 200 and conjugate 11 on Superdex 75.

Small scale conjugate preparative purifications were done on smaller Superdex 200 or Superdex 75 columns (30 cm×0.8 cm², column volume 24 ml, flow rate 0.40 ml/min). Samples of 0.1-0.3 ml were injected and fractions of 0.40 ml were collected.

In the following, conjugates were tested after being purified using crude, rapid and production friendly method of collecting and pooling the void volume fractions (Superdex 75 prep grade gel filtration column, Vo at 42.5 ml). The protein concentration was adjusted to 1.00 mg/ml ($A_{280}$=0.983) and tested for the ability to do affinity purification.

Example 2. Chemo Selective Protein Conjugation Procedure Using SATA and SulfoSMCC The example illustrates an alternative method for preparing TBP using a chemo selective method using Protein A modified with N-succinimidyl S-acetylthioacetate ("SATA") and demasked with hydroxylamine before being coupled with sulfosuccinimidyl 4-(N-maleimidomethyl) cyclohexan-1-carboxylate ("sulfo-SMCC") activated Avidin and purified.

In short, the conjugation unit operations were the same as in the previous detailed described examples.

Protein A (2.6 mg/ml) was activated with SATA (8.8 equivalents in 0.1 M phosphate, 0.15 M NaCl, pH 7.2) for 30 minutes, desalted on a column (PD5, G10), and deacetylated with hydroxyylamine (0.5 M Hydroxylamine, 25 mM EDTA in PBS, pH 7.2) for two hours at room temperature.

The Avidin (5.8 mg/ml) was activated with sulfo-SMCC (9.7 equivalents) in PBS buffer (0.1 M phosphate, 0.15 M NaCl, pH 7.2) for 30 minutes.

Excess cross sulfo-SMCC was removed by passing through a desalting column (25 mM EDTA in PBS, pH 7.2) and collected, before the inter conjugation.

The 1:1 inter conjugation between the thiol modified Protein A (0.5 mg/ml) and maleimido activated avidin (0.8 mg/ml) was done overnight at room temperature at near neutral pH (0.1 M phosphate, 0.15 M NaCl, 5 mM EDTA, pH 7.2.).

The final conjugate solution was cleared by centrifugation at 11.00 G before the TBP was purified on High Prep Sephacryl S-100 as described previously, measured to be about 0.30 mg/ml, called conjugate no. 18 and used in a turbidimetry assay and for purification of immunoglobulin.

The concentration was estimated to be 0.30 mg/ml based on the optical density.

Example 3. Turbidimetry Assay Set Up

Measurement of complex formation was done in a simple turbidimetry assay in a microtiter format using standard ELISA plates and an UV/VIS reader at 340 nm. The assay used Rabbit IgG as target and various TBP molecules. Different concentrations of IgG, TBP and buffer was mixing in the microwells, the change in absorbance at 340 nm recorded over time and the data used for constructing dose-response curves.

In short, the general assay set up was the following:

Six target IgG solutions was diluted (Rabbit IgG, Dako X0903, 20 mg/ml) with buffer (PBS, pH 7.2) to cover the concentration range of interest, typically 0.20 to 7.7 mg/ml in 0.80 ml.

The micro titer plate (NUNC 260836) was prepared by first making the target dilutions and blank, following the addition of the diluted TBP together with different reaction buffers.

Different types of reaction buffer were used: GF: 50 mM HEPES, 150 mM NaCl, pH 7.0 or a PEG containing enhancement buffer (Dako no. S2307).

Target samples (50 µL per well) was pipetted into the wells labelled A to F in the microtitre plate. Dilution buffer (PBS, 50 µL per well) and reaction buffer (175 µL per well) was pipetted into the wells labelled G to H. This was repeated as many times as the number of TBP solutions tested plus one.

At 20 seconds intervals, TBP solution (125 µL) was pipetted using a multi-channel pipette into the wells labelled A to G in the first column, and then pipetted TBP solution (125 µL) into wells labelled A to G in the second column and so forth. The last row in the plate was used as target blank.

The plate was incubated for 10 min at room temperature on a plate mixer and the absorbance read at 1 min intervals. The endpoint was read at 340 nm after 10 minutes.

The collected data, including the blanks, was listed in a spreadsheet and dose response curves plotted as the absorbance at 340 nm versus the target concentration for each TBP concentration.

As a control, Protein A was tested in concentrations from 0 to 1 mg/ml for its ability to form complexes and turbidity with target rabbit IgG. Only a small and insignificant response was observed, confirming that free or unconjugated Protein A did not contribute to the response in the turbidimetry assay of TBP-Target mixtures.

The dose-response curves was used to select the crude and purified TBP molecules of interest and the TBP to target ratio, which was used in the following preparative target purification.

Example 4. Turbidimetry Assay of Crude and Purified Conjugates

The following example illustrates the TBP's ability to form complex and turbidity with the specific target molecule. Further the example illustrates how to select and characterize the TBP prior and after purification based on turbidimetry.

Also, the example illustrates dose-response curves from two TBP's made by two different chemistry methods.

The turbidimetry assay was used to test TBP conjugates prior to purification.

All the crude TBP conjugates was diluted in the standard buffer to approximately 2.0 mg/ml.

FIG. 2 illustrates the dose-response curves at 340 nm after the blank have been subtracted.

All the TBP conjugates (no 2, 3, 6, 7, 8, 9, 10, 12, 13, 14, 15 and 16) gave increased absorbance as a function of increased target concentration. Conjugate No 13, 3 and especially no 12 gave a high response.

Four TBP conjugates, no. 3, 11, 12 and 17 was purified on a Superdex 75 column as described earlier. The conjugates were collected as void volume peaks. Conjugate no 3, 11 and 17 was the mixture of two void volume pools from superdex 75 chromatography purifications.

The purified samples diluted to 1.0 mg/ml and tested in the turdidimetry assay against increasing target concentrations.

Figure 3:
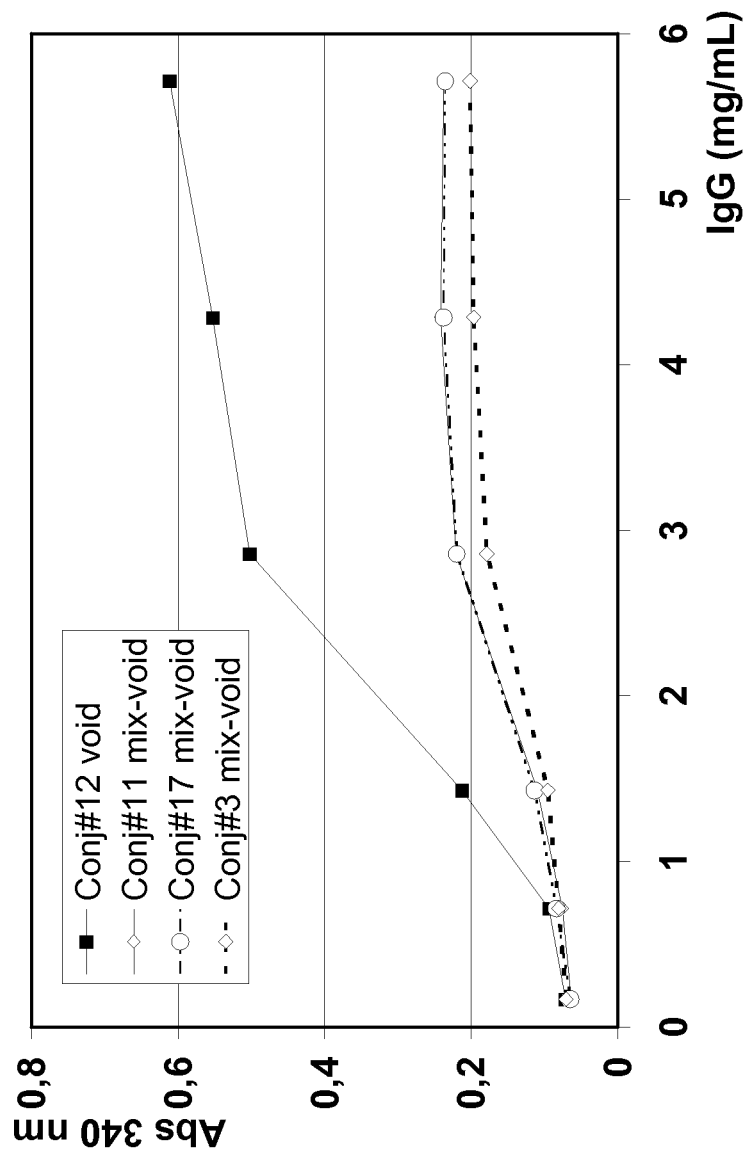
FIG. 3 shows the dose response curve from the turbidimetry assay showing the absorbance at 340 nm versus the IgG concentration for four TBPs after superdex 75 chromatography purification. The conjugates, 3, 11, 12 and 17 were collected as void volume peaks from superdex 75 chromatography purifications. TBP no 3, 11 and 17 was the mixture of two void volume pools. The TBPs was diluted to approximately 1.0 mg/ml.

FIG. 3 illustrates the dose-response curves at 340 nm after the blank have been subtracted. The conjugate #12 again gave the highest response, with an apparent plateau starting after 3.0 mg/ml IgG.

The TBP conjugate no 18 prepared by a SATA-sulfoSPDP conjugation method, as described previously, was tested for its ability to form complexes with target IgG from 0 to 2.75 mg/ml. The TBP solution (0.3 g/L) of 200 μL was reacted with IgG samples (34 μL, 16 μL, 8 μL, 4 μL or 0 μL of Rabbit IgG) (20 g/L).

Figure 4:
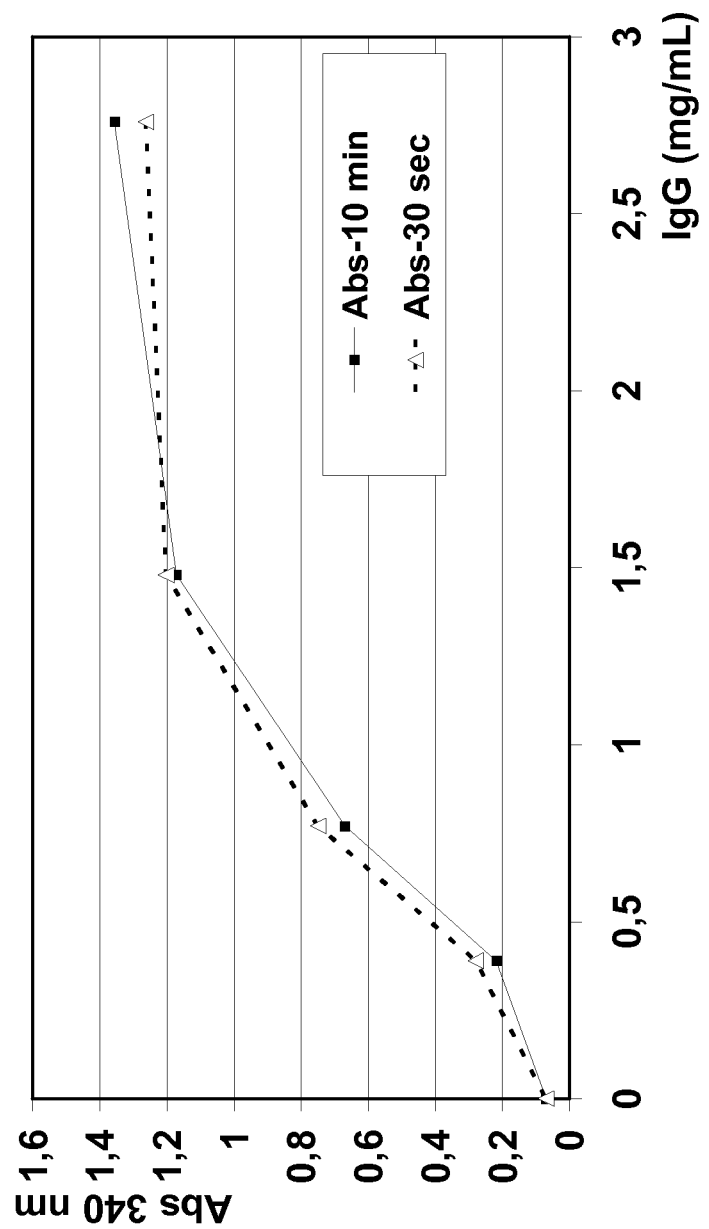
FIG. 4 shows the dose response curve from the turbidimetry assay showing the absorbance at 340 nm after subtraction of blank and after 30 seconds and 10 minutes, against the IgG concentration for TBP no 18 prepared by the SATA/sulfoSPDP metod and diluted to approximately 1.0 mg/ml.

FIG. 4 illustrates the dose-response curves at 340 nm after 30 seconds or 10 minutes, respectively, after the blank have been subtracted. The conjugate shows clear turbidity at the lower target level compared to the previous conjugates.

After recording of the absorbance, the plate with the individual wells was allowed to stand for about one hour. The turbidity changed to be a denser and precipitating cloud in the wells.

Example 5. Turbidimetry Assay with Enhancement Buffer

The example illustrates the use of an enhancement buffer for increasing the complex turbidity between target IgG and TBP.

The turbidimetry assay was performed as described above, except for the dilution of the TBP with (a) the standard buffer (50 mM HEPES, 150 mM NaCl, pH 7.0) or (b) a PEG containing buffer (Dako no. S2307).

TBP no 17 was chosen, as this conjugate gave a lower absorption in the turbidimetry assay compared to e.g. TBP no. 12 (FIG. 3), and therefore is a valid candidate for enhancement.

Conjugate no. 17 (approximately 1.41 mg/ml) was diluted 2-fold with standard buffer or PEG containing buffer resulting in a concentration of 0.70 mg/ml.

In the wells containing the enhancement buffer turbidity a heavy cloudiness' was clearly visible observed after few minutes. The response was recorded over time and the results pictured in FIG. 5.

Figure 5:
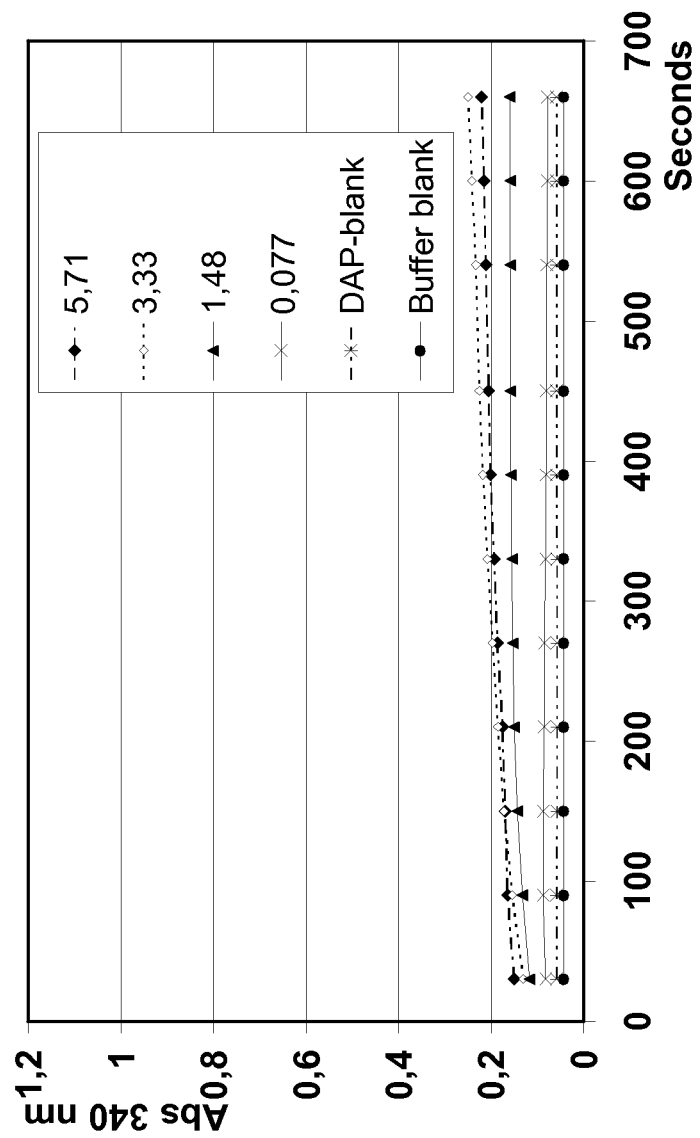
FIG. 5 shows the dose response curve from the turbidimetry assay using the standard buffer showing the absorbance against the time for 5.71; 3.33; 1.48; 0.077 mg/ml target IgG, TBP and buffer blank, respectively.

FIG. 5 is the absorbance using the standard buffer versus the time for 5.71; 3.33; 1.48; 0.077 mg/ml target IgG, TBP and buffer blank, respectively.

Figure 6:
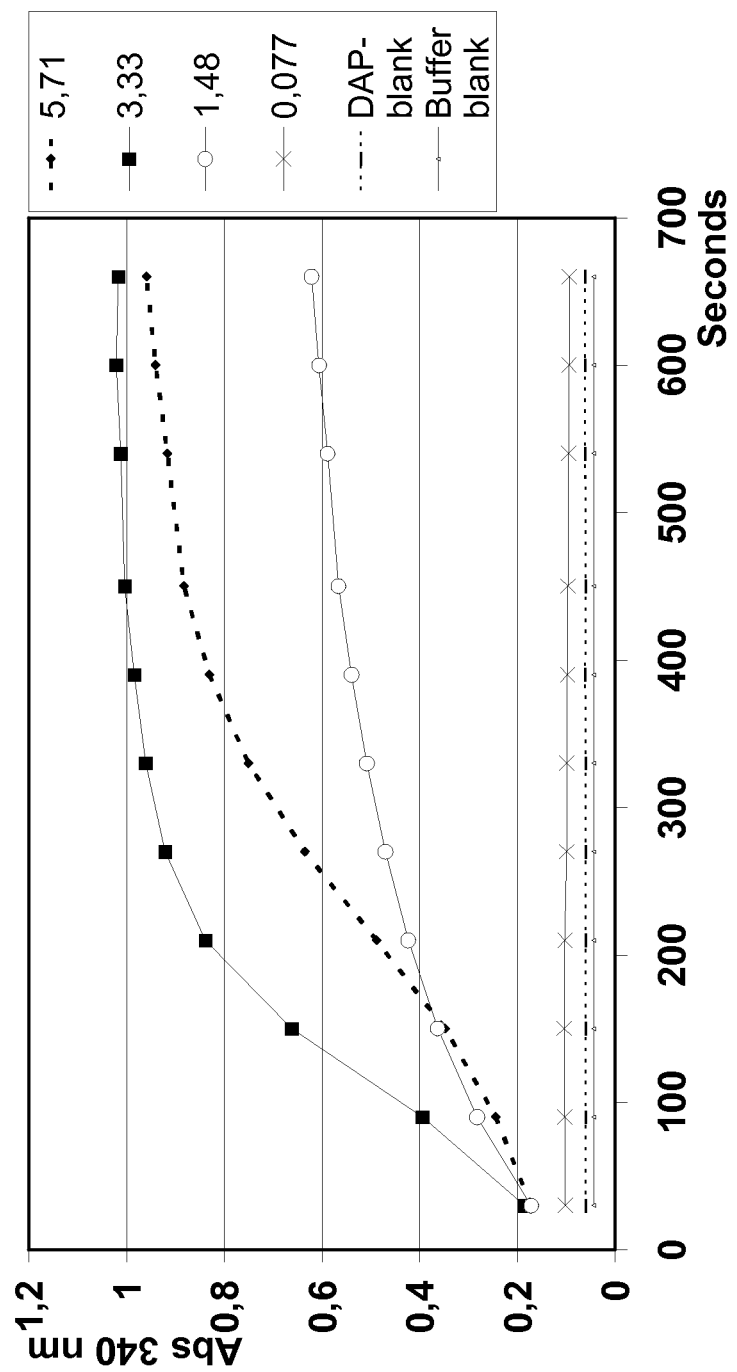
FIG. 6 shows the dose response curve from the turbidimetry assay using the enhancement buffer showing the absorbance against the time for 5.71; 3.33; 1.48; 0.077 mg/ml target IgG, TBP and buffer blank, respectively.

FIG. 6 is the absorbance for the preparation with the enhancement buffer versus the time for 5.71; 3.33; 1.48; 0.077 mg/ml target IgG, TBP and buffer blank, respectively.

Figure 7:
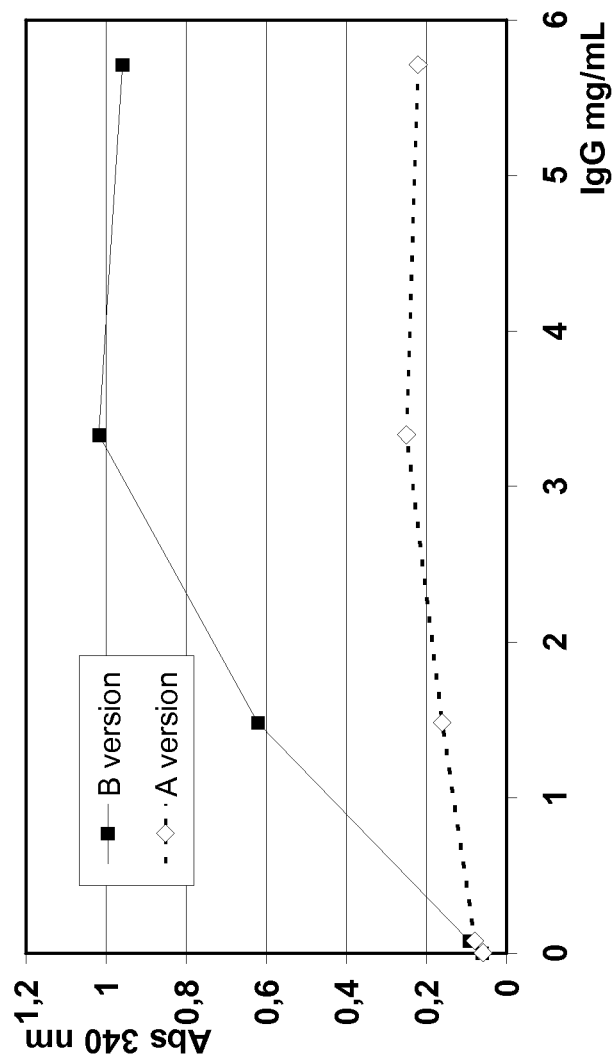
FIG. 7 shows the dose-response curve from the turbidimetry assay showing the absorbance at 340 nm against increasing target concentrations recorded after 10 minutes using (a) the standard HEPES/NaCl pH 7.0 buffer or (b) a PEG containing buffer.

FIG. 7 is the dose-response curve of absorbance against target concentration recorded after 10 minutes using version (a) the standard buffer (50 mM HEPES, 150 mM NaCl, pH 7.0) or version (b) a PEG containing buffer.

After recording of the absorbance, the plate with the individual wells was allowed to stand for up to over night. After a few hours, the turbidity changed to be denser. The next day cloud like precipitates was visible in the wells containing the enhancement buffer.

FIG. 7 clearly illustrates the strong effect of changing the buffer components by adding the PEG containing buffer. The particular TBP conjugate no. 17 was greatly improved with respect to the ability to form complexes with the target in solution.

The following experiments were performed to demonstrate that the TBP molecules prepared by simple chemo selective conjugation of Protein A and Avidin in combination with a simple biotin support material can be used for affinity purification of antibodies.

Example 6. Unspecific Binding to Column

The experiment was performed in order to test for unspecific binding of the IgG target molecule to the simple biotin agarose affinity matrix.

Three 1.0-ml aliquots of biotin-agarose (Sigma Chemicals, product no. B6885) were packed into three identical chromatography columns (Bio-Rad column and flow adaptor, product no. 737-1007 and no. 738-0014), using an equilibration buffer for the packing (0.1 M Na-phosphate, 0.15 M NaCl, pH 7.2). One by one, the three columns with biotin agarose were mounted on an Äkta chromatography system (GE Healthcare), equilibrated, and used for the experiments described below.

1.00 ml gel filtration buffer (0.05 M HEPES, 0.15 M NaCl, pH 7.0) and 0.40 ml IgG, (DAKO product no. X0903 (original 20 mg/ml), 4.3 g/L, 1.4 g/L or 0.7 g/L in equilibration buffer) was applied to each column. The columns was washed with 7.5 ml of equilibration buffer and eluted with 5 ml of elution buffer (0.1 M Na-citrate, pH 3.5) at a flow rate of 1.0 ml/min. Absorbance at 280 nm and conductivity was continuously monitored and recorded.

Table below summarizes the results. The first peak corresponds to the flow through peak and the second peak is the peak during subsequent elution. The percentage distribution between the two peaks is listed.

| IgG conc. g/L | Flow-through peak Area (mAU * ml) | Flow-through peak Area % | IgG peak Area (mAU * ml) | IgG peak Area % |
|---|---|---|---|---|
| 4.3 | 545 | 99 | 4 | 1 |
| 1.4 | 138 | 98 | 3 | 2 |
| 0.7 | 58 | 95 | 3 | 5 |

During elution, fractions of 1 ml were collected and analyzed by SDS-PAGE followed by staining with Coomassie brillant blue. Analysis of the fractions collected during elution showed that pure IgG composed of heavy chain (50 kDa) and light chain (25 kDa) polypeptides was eluted from the column.

No significant binding or subsequent elution of IgG was observed. The IgG concentrations loaded onto the column appeared in the flow-through fraction, indicating that the target molecule IgG does not bind unspecifically to the simple biotin agarose column.

Example 7. Stepwise Affinity Purification in Solution and on Column

The experiment was performed to demonstrate that TBP molecules can be mixed with the target molecule IgG in solution, spontaneously form a complex, be loaded onto a biotin agarose column, and washed thoroughly to remove any contaminants not bound to the column. Finally, by elution at low pH, the target molecules was collected.

TBP conjugate no. 18 (Pooled fractions from High Prep Sephacryl S-100 purification, 0.30 mg/ml) was used in the following.

Based on the previous crude turbidity results, IgG (0.160 ml of 20 mg/ml) and TBP (2.00 ml, 0.30 mg/ml) and 0.04 ml GF buffer (50 mM HEPES, 150 mM NaCl, pH 7.0) was mixed and left for 10 minutes at room temperature. The mixture became visibly turbid during the incubation.

The turbid solution was loaded onto a 1 ml column packed with the biotin-agarose gel. The column was washed with 7.5 ml of equilibration buffer, 18 fraction of 0.50 ml were collected, before the column eluted with 5 ml elution buffer (0.1 M Na-citrate, pH 3.5). The flow through and the elution liquid was recorded at 280 nm in order to estimate peak areas.

As in the previous example, elution fractions were collected and analyzed by SDS-PAGE followed by staining with Coomassie brillant blue. Analysis of the fractions collected during elution showed that pure IgG composed of heavy chain (50 kDa) and light chain (25 kDa) polypeptides was eluted from the column.

The column with bound TBP was used for the capture and elution of IgG. First the column was re-equilibrated as described previously. IgG (0.160 ml IgG 20 mg/ml) and GF buffer (2.04 ml) was mixed and applied to the column, washed and eluted with the Na-citrate buffer as above.

This was repeated eight times on the same column to detect any leakage of bound TBP molecule. The flow through and the elution liquid was again recorded at 280 nm in order to estimate peak areas.

The table below summarizes the flow-through and elution peak areas from the purification (a) in solution and (b) repeated on column.

| | Flow-through peak area (mAU * ml) | Flow-through peak area % | IgG peak area (mAU * ml) | IgG peak area % |
|---|---|---|---|---|
| (a) in solution | 512 | 64 | 286 | 36 |
| (b) on column, injection 1 | 803 | 92 | 73 | 8 |
| (b) on column, injection 2 | 807 | 92 | 71 | 8 |
| (b) on column, injection 3 | 775 | 92 | 68 | 8 |
| (b) on column, injection 4 | 782 | 92 | 69 | 8 |
| (b) on column, injection 5 | 788 | 92 | 68 | 8 |
| (b) on column, injection 6 | 779 | 92 | 66 | 8 |
| (b) on column, injection 7 | 799 | 92 | 68 | 8 |
| (b) on column, injection 8 | 693 | 91 | 66 | 9 |

Figure 8:
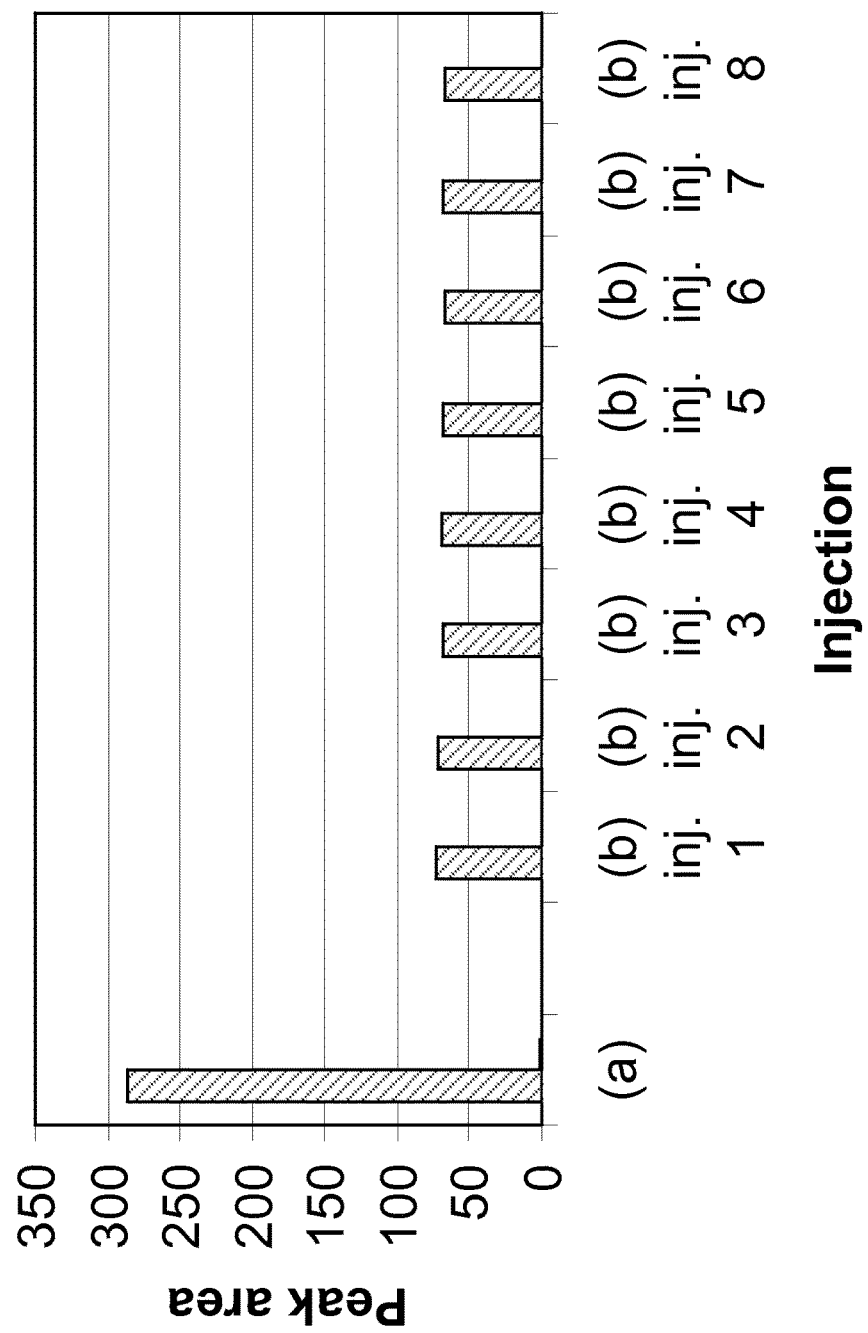
FIG. 8 shows a block diagram comparing the elution IgG peak areas of (a) TBP-Target complex formed in solution and bound to column and (b) from repeated capture and elution of IgG from TBP immobilized to the column prior to IgG capture.

FIG. 8 is a block diagram comparing the elution IgG peak areas from the purification (a) in solution and (b) the repeated elution peaks from TBP bound to the column.

During elution, fractions of 1 ml were collected and analyzed by SDS-PAGE followed by staining with Coomassie brillant blue. Analysis of the fractions collected during elution showed that pure IgG composed of heavy chain (50 kDa) and light chain (25 kDa) polypeptides was eluted from the column.

The results obtained clearly illustrate the relation between complex formation and IgG purification capacity.

The IgG binding capacity for the TBP capture in solution was 4 times higher compared to the same TBP immobilised on the column. The repeated capture-elution cycles shows that no TBP leaks from the column.

Example 8. Stepwise Affinity Purification in Solution and on Column Using an Enhancement Buffer The experiment was performed to demonstrate that TBP molecules can be mixed with the target molecule IgG and an enhancement buffer in solution can form complexes, be applied onto a biotin agarose column, washed and by elution at low pH, the target molecules eluted.

The binding capacity for support bound TBP was compared with or without an enhancement buffer.

Purified TBP conjugate no 17 (about 1.41 mg/ml) prepared by the SPDP/SMCC method was first tested in the turbidimetry assay as described above. Based on the turbidimetry assay with the enhancement buffer, the TBP-to-Target ratio was selected where the dose response curve is reaching a plateau.

Two TBP dilutions were made with the (a) standard GF buffer and with the (b) enhancement buffer containing PEG (Dako, S2307).

TBP (0.475 ml) and buffer (0.475 ml) was mixed. Each mixture was further mixed with IgG (0.20 ml, 20 mg/ml) and incubated at room temperature for 10 minutes.

During the incubation the mixture (b) with the enhancement buffer became turbid, whereas (a) remained transparent.

The TBP-IgG mixtures were loaded on to two identical biotin agarose columns prepared as described previously. As in the previous experiment, the two columns were washed and the IgG eluted with the Na-citrate buffer. The liquid flow from the column was recorded at 280 nm in order to monitor peak areas The two columns with bound TBP were used for the capture and elution of IgG. The column was re-equilibrated as described previously. Mixtures of IgG (0.20 ml IgG 20 mg/ml) and GF buffer (0.95 ml) or enhancement buffer containing PEG (Dako, S2307, 0.95 ml) respectively, was applied to each column, washed and eluted with the Na-citrate buffer as above. The peak areas were measured by recording the UV absorbance at 280 nm of the liquid flow from the column.

The table below summarizes the elution peak areas for the purification of IgG with TBP in solution and bound to the column with the GF and the enhancement buffer, respectively.

|  | TBP in solution Area (mAU * ml) | Immobilized TBP Area (mAU * ml) |
|---|---|---|
| GF standard buffer | 71 | 53 |
| Enhancement buffer | 397 | 81 |

Using the GF buffer, the amount of bound and eluted IgG was about 33% higher for the TBP in solution compared to the column bound TBP.

Also, compared to the GF buffer, the enhancement buffer had some positive effect on the amount of bound and eluted IgG from the column bound TBP.

More significantly, using the enhancement buffer, the amount of bound and eluted IgG was almost 4 times higher for the TBP in solution compared to the column bound TBP.

Example 9. Affinity Purification in Solution, Centrifugation and Removal of TBP

The experiment illustrate the mixing of TBP molecules with the target molecule IgG and enhancement buffer in solution, separation of the formed complex by centrifugation and removal of the TBP on column.

A biotin agarose column is first prepared as described previously, followed by an additional wash with the Na-citrate elution buffer.

TBP conjugate no 17 (about 1.41 mg/ml, 0.95 ml), IgG (0.40 ml, 20 mg/ml) and enhancement buffer (Dako, S2307, 0.95 ml) is mixed for 10 seconds in a (14 ml) polypropylene centrifugal tube with conical bottom. The solution becomes turbid after few minutes. The tube is allowed to stand at room temperature for 60 minutes. The tube is centrigated (10000 rpm, 5 minutes, Ole Dick centrifuge type 157, Copenhagen), and the supernatant removed.

The pellet is washed in precipitation buffer and re-suspended with in Na-citrate elution buffer (2 ml) by mixing with a thin spatula and shaken until the solution is clear. The clear solution is added to the column and the run through liquid monitored by the UV detector and the peak containing the target is collected.

The collected target solution is adjusted to pH 7.

A sample is used for identification of the IgG's heavy chain (50 kDa) and light chain (25 kDa) polypeptide by SDS-PAGE followed by staining with Coomassie brillant blue.

The invention claimed is:

1. A process for purification of a target molecule, comprising the steps: (a) contacting a target molecule, and a population of target binding polypeptides (TBP), in solution for a sufficient time to allow formation of a higher order target-TBP complex; and (b) isolating said target molecule from said higher order target-TBP complex by subsequent purification steps, said isolation of said target molecule from said higher order target-TBP complex being obtained by capturing said higher order target-TBP complexes on a support followed by elution of said target molecule while said TBP remains immobilized to the support wherein (i) said TBP has at least two binding functionalities; a first binding functionality towards said target molecule and a second binding functionality towards a catching ligand comprised in a support, wherein said first and second binding functionalities are different; and (ii) said first binding functionality comprises at least two binding sites for said target molecule, and said target molecule comprises at least two binding sites for said TBP, wherein the ratio of target molecule to TBP is optimized by measuring complex formation, wherein said complex formation is measured by turbidimetry, and wherein said complex formation is equivalent to a change in optical density of at least 0.1 when measured by turbidimetry at 340 nm in a solution of target molecule and TBP, wherein an equilibrium dissociation constant of said TBP towards a target molecule, $K_{D,t}$, is in the range from $10^{-2}$ to $10^{-13}$ M, and an equilibrium dissociation constant of said TBP towards a catching ligand, $K_{D,s}$, is in the range from $10^{-9}$ to $10^{-16}$ M, and wherein the ratio $K_{D,t}/K_{D,s}$ is at least $10^1$, wherein said target molecule is a biomolecule, and wherein said biomolecule is a protein, peptide, oligopeptide, lipoprotein, apolipoprotein, phosphor protein, or glucoprotein.

2. The process according to claim 1, wherein the population of TBPs comprises identical TBPs.

3. The process according to claim 1, wherein the population of TBPs comprises TBPs that are structurally and/or functionally different.

4. The process according to claim 1, wherein the complex formation is performed in the presence of a complex promoting buffer.

5. The process according to claim 4, wherein the buffer comprises reagents for i) lowering the water activity, ii) stabilizing pH and iii) preventing unspecific or random protein interactions and precipitation and increasing the general protein solubility.

6. The process according to claim 5, wherein the reagents for lowering water activity comprises ammonium sulphate, capryllic acid, dextran, poly ethylene glycol (PEG), polyvinyl alcohol (PVA), hyaluronic acid, chitosan and their esters, globular polyols.

7. The process according to claim 6, wherein PEG comprises 1-100 (w/v) PEG with average molecular weight from 1.000 to 10.000 Da.

8. The process according to claim 4, wherein the buffer comprises neutral, anionic, cationic and block-co-polymer detergents or surfactants.

9. The process according to claim 8, wherein the buffer comprises Tween 20, Tween 40, pluronics family or NP40 detergents in concentrations below 2% weight/volume (w/v) of the total solution.

10. The process according to claim 4, wherein pH stabilizing agents comprise phosphate buffers, citrate buffers, borate buffers, and Good buffers.

11. The process according to claim 10, wherein the Good buffers are selected from the group consisting of Tris, Hepes, and MES buffers at pH 5-8.

12. The process according to claim 1, wherein the ratio of target molecule to TBP is optimized to allow optimal complex formation.

13. The process according to claim 1, wherein the first binding functionality comprises at least three binding sites for the target, and/or the target comprises at least three binding sites for the TBP.

14. The process according to claim 1, wherein the at least two or three binding sites comprised in the first binding functionality are functionally different.

15. The process according to claim 1, wherein isolation of the target from the complex is obtained by precipitation or centrifugation, followed by dissolving the complex, capturing the TBP on a solid support, and collecting the target molecule.

16. The process according to claim 1, wherein the biomolecule is an antibody.

17. The process according to claim 6, wherein said globular polyols are ficoll or polyvinyl pyrrolidone (PVP).

* * * * *